United States Patent [19]

Daluge et al.

[11] Patent Number: 4,761,475

[45] Date of Patent: Aug. 2, 1988

[54] 2,4-DIAMINOPYRIMIDINES SUBSTITUTED WITH HETEROBICYCLOMETHYL RADICALS AT THE 5 POSITION USEFUL AS ANTIBACTERIALS

[76] Inventors: Susan M. Daluge, 297 Azalea Dr., Chapel Hill, N.C. 27514; Paul M. Skonezny, 1513 Cotherstone Dr., Durham, N.C. 27712

[21] Appl. No.: 839,463

[22] Filed: Mar. 12, 1986

Related U.S. Application Data

[62] Division of Ser. No. 319,647, Nov. 9, 1981, abandoned.

[30] Foreign Application Priority Data

Nov. 11, 1980 [GB] United Kingdom ............... 8036135

[51] Int. Cl.$^4$ ........................................... C07D 239/49
[52] U.S. Cl. ..................... 544/324; 544/325
[58] Field of Search ............................... 544/324, 325

[56] References Cited

U.S. PATENT DOCUMENTS

| | | | |
|---|---|---|---|
| 3,850,962 | 11/1974 | Grunberg et al. | 544/324 |
| 3,956,327 | 5/1976 | Cresswell et al. | 544/324 |
| 4,039,543 | 8/1977 | Kompis et al. | 544/325 |
| 4,144,263 | 3/1979 | Yeowell et al. | 544/323 |
| 4,258,045 | 3/1981 | Poe et al. | 424/251 |
| 4,279,899 | 7/1981 | Gutsche et al. | 544/324 |

FOREIGN PATENT DOCUMENTS 957797  5/1964  United Kingdom .

OTHER PUBLICATIONS

Yeowell et al., Chem. Abst. 88-104958b.

Primary Examiner—Donald G. Daus
Assistant Examiner—Cecilia Shen
Attorney, Agent, or Firm—Donald Brown

[57] ABSTRACT

Novel 2,4-diaminopyrimidines having substituted heterobicyclomethyl moieties in the 5-position have superior antibacterial properties.

2 Claims, No Drawings

2,4-DIAMINOPYRIMIDINES SUBSTITUTED WITH HETEROBICYCLOMETHYL RADICALS AT THE 5 POSITION USEFUL AS ANTIBACTERIALS

This application is a division of application Ser. No. 319,647, filed Nov. 9, 1981, now abandoned.

The present invention relates to novel 2,4-diamino-5-(substituted)pyrimidines, to pharmaceutical compositions containing them, to processes for preparing them and their compositions, to intermediates for making them and to their use in the treatment of microbial infections.

Certain 2,4-diamino-5-benzylpyrimidines have been demonstrated to be potent inhibitors of dihydrofolate reductase (DHFR) which catalyses the reduction of dihydrofolic acid to tetrahydrofolic acid (THFA). This property has been shown frequently to result in useful pharmaceutical properties particularly in the treatment of bacterial infections. Thus, U.K. Patent Specification No. 875,562 discloses inter alia 2,4-diamino-5-benzylpyrimidines wherein the benzyl moiety is substituted by three $C_{1-4}$ alkoxy groups.

Trimethoprim, 2,4-diamino-5-(3,4,5-trimethoxybenzyl)pyrimidine, is specifically disclosed in U.K. Pat. No. 875,562 and is the most active general antibacterial agent amongst the 2,4-diamino-5-benzylpyrimidines known to date. Due to their mode of action, these benzylpyrimidines potentiate the antibacterial activity of the sulphonamides and trimethoprim has been used extensively over the last decade in human therapy in combination with various sulphonamides, and in particular with sulphamethoxazole, for the treatment of bacterial infections.

Unfortunately, whilst trimethoprim has an excellent level of activity against most aerobic bacteria its activity against anaerobic bacteria is less impressive and its activity against certain aerobic bacteria could beneficially be improved upon. A novel group of 2,4-diamino-5-substituted pyrimidines has now been found many of the compounds having a general level of activity against aerobic bacteria comparable to that of trimethoprim whilst having a superior level of activity against anaerobic bacteria. Some of these compounds are also considerably superior to trimethoprim against gram positive aerobic bacteria, particularly *Staphylococcus aureus* and some compounds have a different pharmacokinetic profile, for example, a longer half life, than trimethoprim.

Accordingly, the present invention provides a compound of the formula (I):

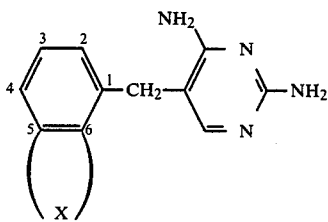

or a salt, N-oxide or acyl derivative thereof, wherein

is a six-membered ring containing a hetero atom, both the phenyl ring the

being optionally substituted except that there are no substituents attached to the atom of

adjacent to the 6-position of the phenyl ring.

The

ring may contain one, two or three double bonds. Suitably the hetero atom is oxygen, nitrogen or sulphur and most suitably it is oxygen or nitrogen.

Substitution of the phenyl ring is preferably at the 3- and/or 4-position with substituents suitably selected from halogen, alkenyl, alkenyloxy, nitro cyano, hydroxy, mercapto, alkylthio, substituted sulphonyloxy, substituted sulphonyl, substituted sulphinyl, or substituted carbonyl, optionally substituted amino, optionally substituted alkyl or optionally substituted alkoxy.

Suitable substitutents of the

ring are selected from halogen, alkylthio, optionally substituted alkyl or alkoxy, gem dimethyl, oxygen or sulphur.

A preferred group of compounds is that of the formula (II):

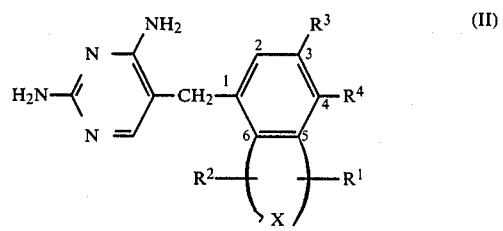

or a salt, N-oxide or acyl derivative thereof, wherein

is a six-membered ring containing three double bonds in which case X is —N═, two double bonds in which case X is —N═ or —NR⁵— or X is —O— adjacent to the 5-position of the phenyl ring, or one double bond in which case X is —NR⁵— wherein $R^5$ is hydrogen, $C_{1-4}$ alkyl or a group —COR⁶ in which $R^6$ is hydrogen, $C_{1-4}$ alkyl, $C_{1-4}$ alkoxy, amino or X is —O— adjacent to the 5-position of the phenyl ring, $R^1$ and $R^2$ are the same or different and each is hydrogen, halogen, $C_{1-4}$ alkyl, $C_{1-4}$ alkylthio or $C_{1-4}$ alkoxy, optionally substituted by halogen, hydroxy or $C_{1-2}$ alkoxy or $R^1$ and $R^2$ are linked to the same carbon atom to form a group C═O, C═S or

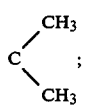

$R^3$ and $R^4$ are the same or different and each is hydrogen, halogen, $C_{2-4}$ alkenyl, $C_{2-4}$ alkenyloxy, nitro, cyano, hydroxy, mercapto, a group —OSO₂R⁷ or —S(O)ₙR⁷ wherein $R^7$ is $C_{1-3}$ alkyl and n is 0, 1 or 2, a group —COR⁸ wherein $R^8$ is methyl, ethyl, methoxy, ethoxy, amino, methylamino, ethylamino, dimethylamino, or diethylamino, or each is amino optionally substituted by one or more $C_{1-4}$ alkyl or $C_{1-4}$ acyl or the nitrogen atom forms part of a five or six membered heterocyclic ring, $C_{1-4}$ alkyl or $C_{1-4}$ alkoxy each optionally substituted by halogen, hydroxy, or $C_{1-2}$ alkoxy, or $R^3$ and $R^4$ together form a methylenedioxy group; except that $R^1$, $R^2$, $R^3$ and $R^4$ are not all hydrogen, that $R^1$ and $R^2$ are not substituents other than hydrogen when attached to the carbon atom adjacent to the 6-position of the phenyl ring and that when X is —O— there is not a halogen atom or an alkoxy group on the carbon atom adjacent to X.

It will be readily apparent that $R^1$ will not be ═O, ═S, or gem dimethyl when

is an aromatic ring. Preferred values for halogen are chlorine and bromine.

Particularly suitable compounds of the formula (II) include those of the formula (III):

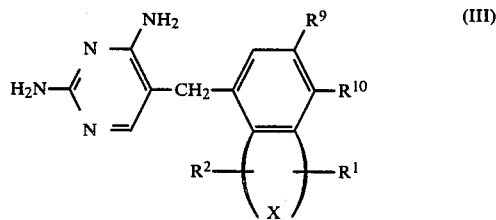

or a salt, N-oxide or acyl derivative thereof wherein

$R^1$ and $R^2$ are as hereinbefore defined and $R^9$ and $R^{10}$ are the same or different and each is hydrogen, halogen, $C_{2-4}$ alkenyl, $C_{2-3}$ alkenyloxy, nitro, a group NR¹¹R¹² wherein $R^{11}$ and $R^{12}$ are the same or different and each is hydrogen, methyl or ethyl or NR¹¹R¹² forms a five or six-membered heterocyclic ring, cyano, hydroxy, a group —S(O)ₙR⁷ or COR⁸ as hereinbefore defined, or $C_{1-4}$ alkyl or $C_{1-4}$ alkoxy each optionally substituted by halogen, hydroxy or $C_{1-3}$ alkoxy, except that $R^9$ and $R^{10}$ are not both hydrogen or halogen, that $R^1$ and $R^2$ are not substituents other than hydrogen when attached to the carbon atom adjacent to the 6-position of the phenyl ring, and that when X is —O— there is not a halogen or alkoxy group on the carbon atom adjacent to X.

Suitably, $R^9$ is $C_{2-3}$ alkenyl, halogen, a group S(O)ₙR⁷ as hereinbefore defined, cyano, amino, mono-$C_{1-3}$-alkyl substituted amino, or $C_{1-3}$ alkyl or $C_{1-3}$ alkoxy each optionally substituted by halogen, hydroxy or $C_{1-3}$ alkoxy.

Most suitably $R^9$ is methoxy, ethoxy, methoxyethoxy, methyl, ethyl, propyl, vinyl, allyl, propenyl, halogen, methylthio, ethylthio. Preferably $R^9$ is methyl, methoxy or ethoxy, particularly methoxy.

Suitably $R^{10}$ is hydrogen, hydroxy, amino, mono- or di-$C_{1-3}$ alkyl substituted amino, nitro, cyano, pyrrolyl, a group —S(O)ₙR⁷ or —COR⁸ as hereinbefore defined or $R^{10}$ is $C_{1-3}$alkoxy optionally substituted by halogen, hydroxy or $C_{1-3}$ alkoxy.

Most suitably $R^{10}$ is hydrogen, hydroxy, methoxy, ethoxy, nitro, amino, methylamino, dimethylamino, ethylamino, diethylamino, methylthio, ethylthio, or pyrrolyl. Preferably $R^{10}$ is methoxy, amino, mono- or dimethylamino or methylthio, particularly methoxy, dimethylamino or methylthio.

Suitably

is an unsaturated six membered ring in which X is —O— adjacent to the 5-position of the phenyl ring or —N═. Suitably when X is —N═ this is α, β or δ to the 5-position of the phenyl ring and preferably α or β to the 5-position of the phenyl ring.

Suitably $R^1$ is hydrogen, gem dimethyl, $C_{1-3}$ alkyl optionally substituted by halogen, $C_{1-3}$-alkylthio or $C_{1-3}$ alkoxy optionally substituted by halogen, hydroxy or $C_{1-2}$ alkoxy. Most suitably $R^1$ is hydrogen, methyl, trifluoromethyl or methoxy and preferably $R^1$ is hydrogen.

Suitably $R^2$ is hydrogen, $C_{1-3}$ alkyl, optionally substituted by halogen, $C_{1-3}$-alkylthio or $C_{1-3}$ alkoxy optionally substituted by halogen, hydroxy or $C_{1-2}$ alkoxy. Most suitably $R^2$ is hydrogen, methyl, trifluoromethyl or methoxy and preferably $R^2$ is hydrogen.

Preferably only one of $R^1$ and $R^2$ is other than hydrogen when X is —O—, —N= or —NR$^5$—.

One group of preferred compounds of the present invention includes those of the formula (IV):

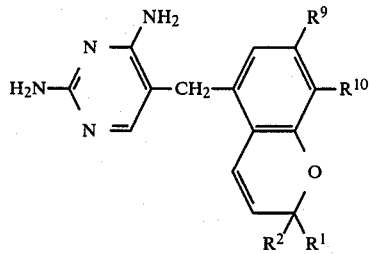

or a salt, N-oxide or acyl derivative thereof wherein $R^1$, $R^2$, $R^9$ and $R^{10}$ are as hereinbefore defined except that $R^9$ and $R^{10}$ are not both hydrogen or halogen. Suitably $R^1$ is hydrogen or methyl, and preferably $R^1$ is hydrogen. Suitably $R^2$ is hydrogen or methyl. Suitably $R^9$ is methoxy, ethoxy or methylthio. Preferably $R^9$ is methoxy or ethoxy. Suitably $R^{10}$ is hydrogen, methoxy, ethoxy, methylthio or a group $NR^{13}R^{14}$ in which $R^{13}$ and $R^{14}$ are the same or different and each is hydrogen, methyl or ethyl or $NR^{13}R^{14}$ forms a pyrrolyl group. Most suitably $R^{10}$ is methoxy, ethoxy, dimethylamino, diethylamino or pyrrolyl. Preferably $R^{10}$ is methoxy or ethoxy.

A further group of preferred compounds of the present invention is that of the formula (V):

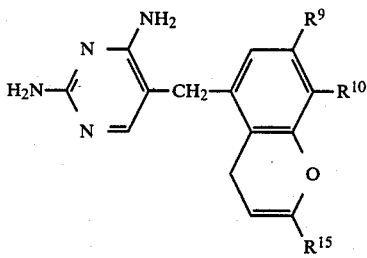

or a salt, N-oxide or acyl derivative thereof, wherein $R^9$ and $R^{10}$ are as hereinbefore defined except that $R^9$ and $R^{10}$ are not both hydrogen or halogen and $R^{15}$ is a hydrogen atom or a $C_{1-3}$ alkyl group.

Suitable values of $R^9$ and $R^{10}$ are those defined in formula (IV). Suitably $R^{15}$ is hydrogen or methyl and preferably $R^{15}$ is hydrogen.

A further group of preferred compounds of the present invention is that of the formula (VI):

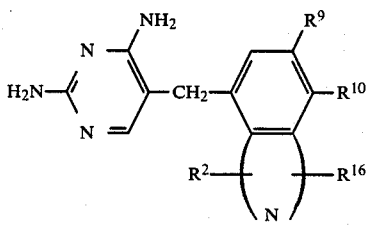

or a salt, N-oxide or acyl derivative thereof,

is a six membered heterocyclic ring containing nitrogen and $R^2$, $R^9$ and $R^{10}$ are as hereinbefore defined and $R^{16}$ is hydrogen, halogen, $C_{1-3}$ alkylthio, $C_{1-3}$ alkyl or $R^{16}$ is $C_{1-3}$ alkoxy optionally substituted by halogen, hydroxy or $C_{1-2}$ alkoxy except that $R^9$ and $R^{10}$ are not both hydrogen or halogen and that $R^2$ and $R^{16}$ are not attached to the carbon atom adjacent to the 6-position of the phenyl ring. Suitably

is an aromatic six membered ring containing nitrogen.

Suitable compounds of the formula (VI) are those wherein the nitrogen atom is $\alpha$-, $\beta$- or $\delta$- to the 5-position of the phenyl ring and most suitably those wherein the nitrogen atom is $\alpha$- or $\beta$- to the 5-position of the phenyl ring.

Suitably $R^2$ is hydrogen, methyl, trifluoromethyl, methylthio or methoxy, most suitably $R^2$ is hydrogen or methyl and preferably $R^2$ is hydrogen.

Suitably $R^{16}$ is hydrogen, methyl, methylthio or methoxy, and preferably $R^{16}$ is hydrogen.

Suitably $R^9$ is methoxy, ethoxy, $C_{2-3}$ alkenyl, halogen, $C_{1-3}$ alkyl or methylthio.

Most suitably $R^9$ is methyl, methoxy, ethoxy or methylthio and preferably $R^9$ is methyl, methoxy or ethoxy.

Suitably $R^{10}$ is methoxy, ethoxy, methylthio or a group $NR^{13}R^{14}$ as hereinbefore defined. Preferably $R^{10}$ is methoxy, ethoxy, amino, dimethylamino or methylthio.

A particularly preferred group of compounds of the formula (VI) is that where nitrogen atom is $\alpha$- to the 5-position of the phenyl ring, $R^2$ and $R^{16}$ are hydrogen, $R^9$ is methyl or methoxy and $R^{10}$ is amino, dimethylamino or methylthio.

One group of compounds within the general formula (I) included within the scope of the present invention is that of the formula (VII):

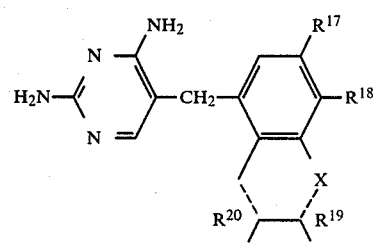

or a salt or acyl derivative thereof, wherein $R^{17}$ and $R^{18}$ together form a methylene-dioxy group or $R^{17}$ is hydrogen, halogen, $C_{1-4}$ alkyl, $C_{1-4}$ alkoxy, $C_{2-4}$ alkenyl, amino, substituted amino, trifluoromethyl, a group —COR$^{21}$ wherein $R^{21}$ is $C_{1-4}$ alkyl or $C_{1-4}$ alkoxy, or a group —OSO$_2$R$^{22}$ wherein $R^{22}$ is $C_{1-4}$ alkyl; $R^{18}$ is halogen, $C_{1-4}$ alkyl, $C_{1-4}$ alkoxy, $C_{2-4}$ alkenyl, hydroxy, amino, mono- or di-$C_{1-4}$ alkyl substituted amino, mercapto, $C_{1-4}$ alkylthio, trifluoromethyl, a group —$COR^{21}$ or a group —$OSO_2R^{22}$ wherein $R^{21}$ and $R^{22}$ are as hereinbefore defined; $R^{19}$ is hydrogen =O, =S, $(CH_3)_2$, halogen, $C_{1-4}$ alkyl; $R^{20}$ is hydrogen or methyl, X is oxygen, nitrogen or an —NH— group and the dotted lines represent single or double bonds with the exception that when X is oxygen atom the dotted line adjacent to it cannot represent a double bond.

Preferred compounds of the present invention include:

2,4-diamino-5-(7,8-dimethoxy-2H-1-benzopyran-5-ylmethyl)pyrimidine, 2,4-diamino-5-(3,4-dihydro-7,8-dimethoxy-2H-1-benzopyran-5-ylmethyl)pyrimidine, 2,4-diamino-5-(8-methoxy-5-quinolylmethyl)pyrimidine, 2,4-diamino-5-(7,8-dimethoxy-2-methyl-2H-1-benzopyran-5-ylmethyl)pyrimidine, 2,4-diamino-5-(7,8-dimethoxy-2,2-dimethyl-2H-1-benzopyran-5-ylmethyl)pyrimidine, 2,4-diamino-5-(8-amino-7-methyl-5-quinolylmethyl)pyrimidine, 2,4-diamino-5-(7,8-dimethoxy-2-oxo-2H-1-benzopyran-5-ylmethyl)pyrimidine, 2,4-diamino-5-(7,8-dimethoxy-2-methyl-4H-1-benzopyran-5-ylmethyl)pyrimidine, 5-(7-allyl-8-hydroxy-2-methyl-5-quinolylmethyl)-2,4-diaminopyrimidine, 5-(7-allyl-8-hydroxy-5-quinolylmethyl)-2,4-diaminopyrimidine, 5-(7-allyl-8-methoxy-5-quinolylmethyl)-2,4-diaminopyrimidine, 2,4-diamino-5-(8-methoxy-7-(1-propenyl)-5-quinolylmethyl)pyrimidine, 5-(7-allyl-8-methoxy-2-methyl-5-quinolylmethyl)-2,4-diaminopyrimidine, 2,4-diamino-5-(8-amino-7-methoxy-5-quinolylmethyl)pyrimidine, 2,4-diamino-5-(8-dimethylamino-7-methoxy-5-quinolylmethyl)pyrimidine, 2,4-diamino-5-(8-(1-pyrrolyl)-7-methyl-5-quinolylmethyl)pyrimidine, 2,4-diamino-5-(8-dimethylamino-7-methyl-5-quinolylmethyl)pyrimidine, 2,4-diamino-5-(8-methoxy-7-propyl-5-quinolylmethyl)pyrimidine, 2,4-diamino-5-(8-hydroxy-7-methoxy-5-quinolylmethyl)pyrimidine, 5-(7-allyl-8-methoxy-5-(1,2,3,4-tetrahydroquinolyl)methyl)-2,4-diaminopyrimidine, 2,4-diamino-5-(7,8-dimethoxy-2H-1-benzopyran-5-ylmethyl)pyrimidine-1-oxide, 2,4-diamino-5-(7-methoxy-8-nitro-5-quinolylmethyl)pyrimidine, 2,4-diamino-5-(7,8-dimethoxy-5-quinolylmethyl)pyrimidine, 2,4-diamino-5-(7-methyl-5-quinolylmethyl)pyrimidine, 4-amino-5-(7,8-dimethoxy-2-H-1-benzopyran-5-ylmethyl)-2-glycinamidopyrimidine, 2,4-diamino-5-(8-amino-7-ethoxy-5-quinolylmethyl)pyrimidine, 2,4-diamino-5-(8-amino-7-methylthio-5-quinolylmethyl)pyrimidine, 2,4-diamino-5-(8-amino-7-chloro-5-quinolylmethyl)pyrimidine, 2,4-diamino-5-(7-methoxy-5-quinolylmethyl)pyrimidine, 2,4-diamino-5-(7-methoxy-8-methylthio-5-quinolylmethyl)pyrimidine, 5-[7-allyl-8-(2-methoxyethoxy)-5-quinolylmethyl]-2,4-diaminopyrimidine, 2,4-diamino-5-(5-amino-6-methyl-8-quinolylmethyl)pyrimidine, 2,4-diamino-5-(5-amino-6-methoxy-8-quinolylmethyl)pyrimidine, 2,4-diamino-5-(8-amino-7-methoxy-5-isoquinolylmethyl)pyrimidine, 2,4-diamino-5-(7,8-dimethoxy-4H-1-benzopyran-5-ylmethyl)pyrimidine, or a salt or N-oxide thereof.

Suitably the compounds of the formula (I) to (VII) are present in the form of the free base or an acid addition salt thereof.

Some compounds of the formula (I) exist in isomeric forms. The present invention includes mixtures of the isomeric forms as well as the individual isomers.

Certain compounds of the formula (I) whilst having some antibacterial activity in their own right are also useful as intermediates in the preparation of other compounds of the formula (I) having interesting antibacterial activity.

The compounds of the formula (I) are bases and, as such, form acid addition salts with acids. Suitable acid addition salts of the compounds of the formula (I) include those formed with both organic and inorganic acids. Such acid addition salts will normally be pharmaceutically acceptable. Thus, preferred salts include those formed from hydrochloric, sulphuric, citric, tartaric, phosphoric, lactic, benzoic, glutamic, aspartic, pyruvic, acetic, succinic, fumaric, maleic, oxaloacetic, isethionic, stearic, fumaric, methanesulphonic, toluene p-sulphonic, lactobionic and glucuronic acids.

When the compounds of the formula (VI) are substituted by hydroxy groups, alkali metal salts of these compounds may be formed and these salts also comprise part of the present invention. Particularly suitable alkali metal salts are those formed with sodium and potassium.

Suitable acyl derivatives are those wherein an amino group is substituted by a group —COM wherein M is hydrogen or $C_{1-11}$ alkyl or $C_{2-11}$ alkenyl, preferably $C_{1-4}$ alkyl or $C_{2-4}$ alkenyl, optionally substituted by carboxy, carb-$C_{1-4}$ alkoxy, nitrile, amino, chlorine or phenoxy optionally substituted by halogen, methyl or methoxy, the alkyl or alkenyl groups being optionally interspersed with one or more oxygen atoms or forming part or the whole of a cycloaliphatic ring or M may represent a $C_{6-10}$ aromatic or $C_{6-10}$ araliphatic residue optionally substituted by one or more chlorine atoms or methyl, $OCH_2COOH$, carb-$C_{1-4}$ alkoxy or a heterocyclic group containing one or more nitrogen, oxygen or sulphur atoms.

Preferred acyl derivatives are those wherein the amino group at the 2-position of the pyrimidine ring is substituted, particularly those wherein the amino group is substituted by acetyl or by an acyl group derived from an amino acid such as a glycyl group.

Suitable N-oxides of compounds of the formula (I) include those formed by oxidation of either or both of the nitrogen atoms in the pyrimidine ring or by oxidation of X when this is a nitrogen atom.

The preparation of salts, acyl derivatives and N-oxides is carried out by conventional methods well known to those skilled in the art.

Pharmaceutically acceptable acid addition salts of compounds of the formula (I) form a particularly preferred aspect of the present invention.

In a further aspect, the present invention provides a pharmaceutical composition comprising a compound of the formula (I) in a combination with a pharmaceutically acceptable carrier. By the terms "pharmaceutical composition" and "pharmaceutically acceptable carrier" are meant those compositions and carriers suitable for use in human and/or veterinary medicine.

The compounds of the formula (I) can conveniently be presented in the compositions of the present invention in an effective unit dosage form, that is to say in an amount sufficient to be effective against the bacterial organism in vivo.

The pharmaceutically acceptable carriers present in the compositions of the present invention are materials recommended for the purpose of administering the medicament. These may be liquid, solid or gaseous materials, which are otherwise inert or medically acceptable and are compatible with the active ingredient.

These pharmaceutical compositions may be given parenterally, orally, used as a suppository, applied as an ophthalmic solution, or applied topically as an ointment, cream or powder. However, oral and parenteral administration of the compositions is preferred for human use. For veterinary use, intramammary as well as oral and parenteral administration is preferred.

For oral administration, fine powders or granules will contain diluting, dispersing and/or surface active agents, and may be presented in a draught, in water or in a syrup, in capsules or cachets in the dry state or in a non-aqueous suspension wherein suspending agents may be included, or in a suspension in water or syrup. Where desirable or necessary, flavouring, preserving, suspending, thickening or emulsifying agents can be included.

For parenteral administration, the compounds may be presented in sterile aqueous injection solutions which may contain antioxidants or buffers.

As stated above, free base or a salt thereof may be administered in its pure form unassociated with other additives in which case a capsule or cachet is the preferred carrier.

Other compounds which may be included are, for example, medically inert ingredients, e.g. solid and liquid diluents such as lactose, glucose, starch or calcium phosphate for tablets or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Alternatively the active compound may be presented in a pure form as an effective unit dosage, for instance, compressed as a tablet or the like.

For veterinary use, different intramammary formulations will normally be prepared for use in dry cows and for use in milking cows. Thus, formulations for dry cow use will normally be in an oil, such as peanut oil, gelled with a gelling agent such as aluminium monostearate. Formulations for milking cow use will usually contain an emulsifying agent (for example Tween 20 or a polysorbate) and a milk miscible carrier such as peanut oil or a mineral oil.

It may be advantageous to include the compounds of formula (I) in a pharmaceutical composition which includes other active ingredients for example p-aminobenzoic acid competitors such as sulphonamides.

Of known p-aminobenzoic acid competitors, the following sulphonamide compounds (or pharmaceutically acceptable salts thereof) are particularly useful:

Sulfanilamide, Sulfadiazine, Sulfamethisazole, Sulfapyridine, Sulfathiazole, Sulfamerazine, Sulfamethazine, Sulfisoxazole, Sulformethoxine, 2-(p-Aminobenzene)-sulfonamide-3-methoxypyrazine (Kelfizina), Sulfony Idianiline, Mafenide,5-Sulfanilamido-2,4-dimethyl pyrimidine, 4-($N^1$-Acetylsulfanilamido)-5,6-dimethoxy pyrimidine, 3-Sulfanilamido-4,5-dimethyl isoxazole, 4-Sulfanilamido-5-methoxy-6-decyloxy pyrimidine sulfamono-methoxine, 4-p-(8-Hydroxy quinolinyl-4-azo)-phenylsulfanilamido-5,6-dimethoxy pyrimidine, Sulfadimethoxine, Sulfadimidine, Sulfamethoxazole Sulfamoxole, Sulfadoxine, Sulfaguanidine, Sulfathiodimethoxine, Sulfaquinoxaline, and p-(2-Methyl-8-hydroxyquinolinyl-5-azo)phenyl sulfanilamido-5,6-dimethoxy pyrimidine.

However, the most preferred combinations include those containing Sulfadiazine, Sulfamethoxazole, Sulfadoxine, Sulfamoxole or Sulfadimidine. The ratio of the compound of the formula (I) to sulphonamide will normally be from 3:1 to 1:10, for example 1:1 to 1:5. A particularly preferred composition of the present invention comprises a compound of formula (I) and a sulphonamide in a ratio of 1:2 to 1:5 preferably together with a pharmaceutically acceptable carrier.

Tablets or other forms of presentation provided in discrete units may conveniently contain an amount of compound of the formula (I) which is effective at a dosage or as a multiple of the same, for instance for human use, units containing 2.5 to 200 mg usually around 30 to 100 mg, for veterinary use, units containing 30 to 500 mg.

The pharmaceutical compositions of the present invention can be prepared by the admixture of a compound of the formula (I) with a pharmaceutically acceptable carrier. Other active ingredients, such as a sulfonamide, or conventional pharmaceutical excipients may be admixed as required.

The compounds of the present invention are useful for the treatment of gram negative aerobic, gram positive aerobic or anaerobic bacterial infections in mammals. They are particularly useful in the treatment of Staphylococcal infections for example mastitis in cattle, Neisseria infections in humans, for example *N. gonorrhea*, acne in humans, and anaerobic infections. Most compounds also have an excellent level of general antibacterial activity.

Still another aspect of the present invention provides a method for the treatment or prophylaxis of bacterial infections in mammals by the administration of an effective non-toxic antibacterial amount of a compound of formula (I) or a pharmaceutically acceptable salt thereof, or a composition as hereinbefore described.

As indicated above, the compounds of the formula (I) are generally useful in treating bacterial infections by rectal, parenteral, topical or oral administration. The compounds of formula (I) are nornally administered at a dose from 0.1 mg/kg to 30 mg/kg per day and preferably 1 mg/kg to 10 mg/kg. The dose range for adult humans is generally from 25 to 300 mg/kg and preferably 100 to 200 mg/day.

The dose range for intramammary administration of the compounds of the formula (I) is generally from 100 to 500 mg, preferably 200 mg to 400 mg, per quarter of the udder to dry cows. Milking cows will normally receive four to six medications of a composition of the present invention, a dose being conveniently administered at milking time (i.e. twice daily) to each of the desired quarters of the udder. Dry cows will normally receive only one medication of a composition of the present invention, one dose being provided to each of the four quarters of the udder.

The compounds of formula (I) and their pharmaceutically acceptable salts may be prepared by methods known for the synthesis of compounds of analogous structure.

Thus the present invention provides a process for preparation of compounds of the formula (I) as hereinbefore defined which process comprises:

(a) (i) the reaction of a guanidine salt with a compound of the formula (VIII) or (IX):

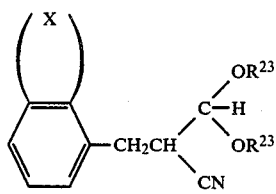 (VIII)

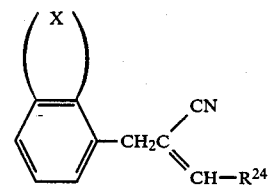 (IX)

wherein

is as hereinbefore defined, and the phenyl and

rings are each optionally substituted as hereinbefore defined $R^{23}$ is a $C_{1-4}$ alkyl group and $R^{24}$ is a nucleophilic leaving group such as $C_{1-4}$ alkoxy group or an amino, $C_{1-4}$ alkylamino, benzylamino, di-$(C_{1-4})$alkylamino, naphthylamino, optionally substituted anilino, morpholino, pipridino or N-methyl piperazino group and most preferably $R^{24}$ is an anilino group:

(ii) the reaction of a compound of the formula (X):

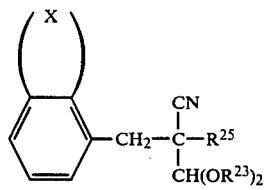 (X)

wherein

and $R^{23}$ are as hereinbefore defined and the phenyl and

rings are each optionally substituted as hereinbefore defined and $R^{25}$ is an alkoxycarbonyl or aldehyde group, with potassium or sodium hydroxide in a $C_{1-4}$ alkanol followed by addition of guanidine;

(iii) the reaction of a compound of the formula (XI):

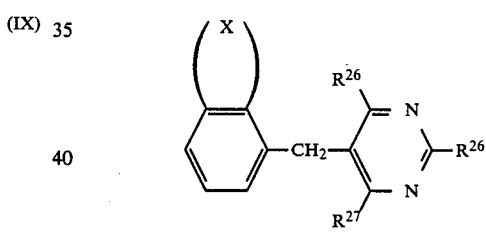 (XI)

wherein $R^{26}$ is an amino group or a leaving group, such as a $C_{1-4}$ alkylthio group or a halogen atom, $R^{27}$ is a hydrogen or halogen atom, except that both groups $R^{26}$ cannot be amino groups and

is as hereinbefore defined and the phenyl and

rings are each optionally substituted as hereinbefore defined with an aminating agent such as ammonia and thereafter when $R^{27}$ is a halogen atom removing this by hydrogenolysis;

(iv) the reaction of a compound of the formula (XII):

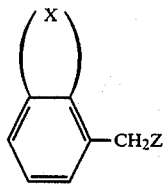

wherein Z is a halogen atom and

is as hereinbefore defined and the phenyl and

rings are each optionally substituted as hereinbefore defined or Z is hydroxy or di-$C_{1-4}$ alkyl substituted amino, and the 4-position of the phenyl ring is substituted by hydroxy, amino, or mono or di-$C_{1-4}$ alkyl substituted amino and the phenyl and

rings each being optionally substituted by other substituents as hereinbefore defined with a compound of the formula (XIII):

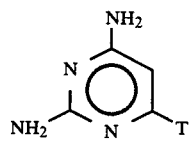

wherein T is a hydroxy or $C_{1-4}$ alkylthio group, and then converting the group T to hydrogen by hydrogenolysis when T is a $C_{1-4}$ alkylthio group or, when T is a hydroxy group, by first converting it to the mesylate or tosylate derivative or to thio, alkylthio or halogen and then removing this by hydrogenolysis;

(b) when it is required to prepare a compound of the formula (IV), (i) the β-elimination of the group Y from a compound of the formula (XIV):

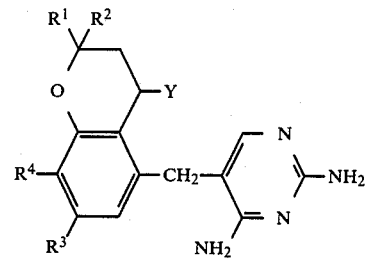

wherein $R^1, R^2, R^3$ and $R^4$ are as hereinbefore defined and Y is a leaving group such as hydroxy, substituted sulphonyloxy, for example mesyloxy, or tosyloxy, alkylthio, phenylthio or halogen.

(ii) the cyclisation of a compound of formula (XV)

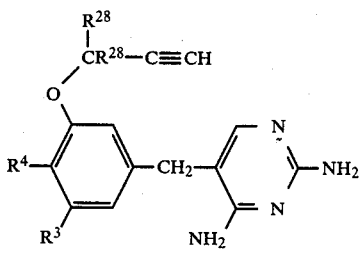

wherein $R^3$ and $R^4$ are as hereinbefore defined and the two groups $R^{28}$ are the same or different and each is hydrogen or $C_{1-4}$ alkyl.

(c) when it is required to prepare a compound of the formula (I) wherein the 4-position of the phenyl ring is substituted by hydroxy, amino or substituted amino the reaction of a compound of the formula (XVI):

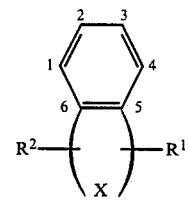

wherein the 4-position of the phenyl ring is substituted by hydroxy, amino, substituted amino and the phenyl and

rings each being optionally substituted by other substituents as hereinbefore defined with 2,4-diamino-5-hydroxymethylpyrimidine.

(d) the conversion of one compound of the formula (I) to a different compound of the formula (I), for example by the reduction or isomerisation of one or two double bonds, conversion of a hydroxy group to a $C_{1-4}$ alkylthio group or an optionally substituted $C_{1-4}$ alkoxy group or conversion of an amino group to a $C_{1-4}$ alkylthio group or hydrogen, halogen, hydroxy or cyano via a diazo group or to a substituted amino group by methods well known to those skilled in the art. The isomerisation of a compound of the formula (IV) to a compound of the formula (V) is conveniently carried out in an aprotic solvent in the presence of a strong base such as potassium t-butoxide.

The reaction of guanidine with a compound of the formula (VIII) or (IX) will take place under conditions analogous to those described in U.K. Pat. Nos. 1 133 766 and 1 261 455 respectively for the preparation of structurally related benzylpyrimidines. Conveniently the reaction is carried out in a $C_{1-4}$ alkanol, for example methanol or ethanol. The compounds of the formula (VIII) and (IX) may be prepared by methods known in the art. It is preferred to avoid the use of aprotic solvents in the preparation of compounds of the formula (VIII) when X is oxygen.

The reaction of a compound of the formula (X) with guanidine and the preparation of the compounds of the formula (X) will be carried out by methods analogous to those described in Belgian Pat. No. 855 505.

In the compounds of the formula (XI) when $R^{26}$ or $R^{27}$ are halogen atoms these are suitably chlorine or bromine atoms. The reaction may conveniently be carried out under the reaction conditions described in U.K. Pat. Nos. 875 562 and 1 132 082. The reduction of $R^{27}$ when this is halogen will suitably be carried out under the conditions described in German Offenlegungsschrift No. 2258238. This is not a preferred method for preparing those compounds wherein $R^3$ or $R^4$ are groups that are susceptible to catalytic hydrogenation.

The compounds of formula (XI) may be prepared by methods known in the art, for example as described in U.K. Pat. Nos. 875562 and 1132082 or German Offenlegungsschrift No. 2258238. The compounds of the formula (XI) wherein $R^{26}$ and/or $R^{27}$ are halogen atoms may conveniently be prepared from the corresponding compounds wherein $R^{26}$ and/or $R^{27}$ are hydroxy. These compounds may be prepared by methods analogous to these described in the art or by the reaction of a compound of the formula (XVI) with 5-dimethylaminomethyluracil. This reaction will normally be carried out in an inert high boiling polar solvent, for example a high boiling $C_{2-6}$ alkanol such as ethylene glycol, at between 100° and 200° C. for example between 130° and 160° C. The reaction will normally be carried out under basic conditions when the 4-position of the phenyl ring is substituted by hydroxy, for example in the presence of sodium methoxide, and under neutral conditions when the 4-position of the phenyl ring is substituted by amino or substituted amino.

Certain compounds of the formula (XI) wherein the 4-position of the phenyl ring is substituted by a hydroxy group may be converted to compounds of the formula (XI) wherein is substituted by an alkoxy or $C_{1-4}$ alkylthio group and certain compounds of the formula (XI) wherein the 4-position of the phenyl ring is substituted by an amino group and $R^{26}$ is a hydroxyl group may be converted to compounds of the formula (XI) wherein the 4-position of the phenyl ring is substituted by $C_{1-4}$ alkyl thio, halogen, cyano, substituted amino group or hydrogen by methods well known to those skilled in the art.

Suitably Z is a dialkylamino or cyclic amino group containing up to 10 carbon atoms; a dimethylamino group is particularly convenient. The reaction will be carried out under conditions well known to those skilled in the art of Mannich reactions. It has been found that the reaction may suitably be carried out at an elevated temperature, suitably between 100° C. and 200° C. in a solvent having a suitably high boiling point, for example a glycol such as ethylene glycol. The dethiation is suitably carried out by hydrogenolysis in the presence of a transition metal catalyst; Raney nickel is particularly suitable for this purpose. This reaction will normally be carried out in a polar solvent, for example a $C_{1-4}$ alkanol such as methanol or ethanol.

Again, this is not a preferred method of preparing those compounds of the formula (I) wherein there are groups that are susceptible to a catalytic hydrogenation.

Preferably Y is a hydroxy group in which case the elimination reaction will be carried out under acidic conditions. Substituted sulphonyloxy groups can also be removed under basic conditions. Halogen atoms are normally removed under basic conditions.

The dehydration of a compound of the formula (XIV) when Y is a hydroxy group will normally take place in the presence of a solvent. $C_{2-4}$ Alkanols are particularly suitable solvents for use in this reaction. The acidic conditions will normally be provided by a strong acid such as a mineral acid. Hydrochloric acid has been found to be particularly suitable for this purpose.

The compounds of the formula (XIV) wherein $R^1$ and $R^2$ are hydrogen and Y is OH may be prepared by the following reaction scheme:

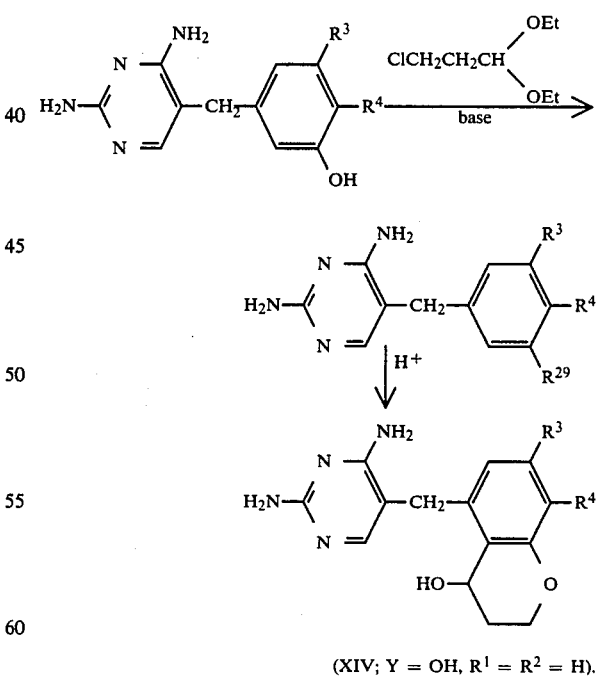

(XIV; Y = OH, $R^1 = R^2 = H$).

The compounds of the formula (XIV) wherein Y is hydroxy and $R^1$ and $R^2$ are attached to the carbon atom adjacent to the ring oxygen atom and are the same or different and each is hydrogen or methyl may be prepared by the following reaction scheme:

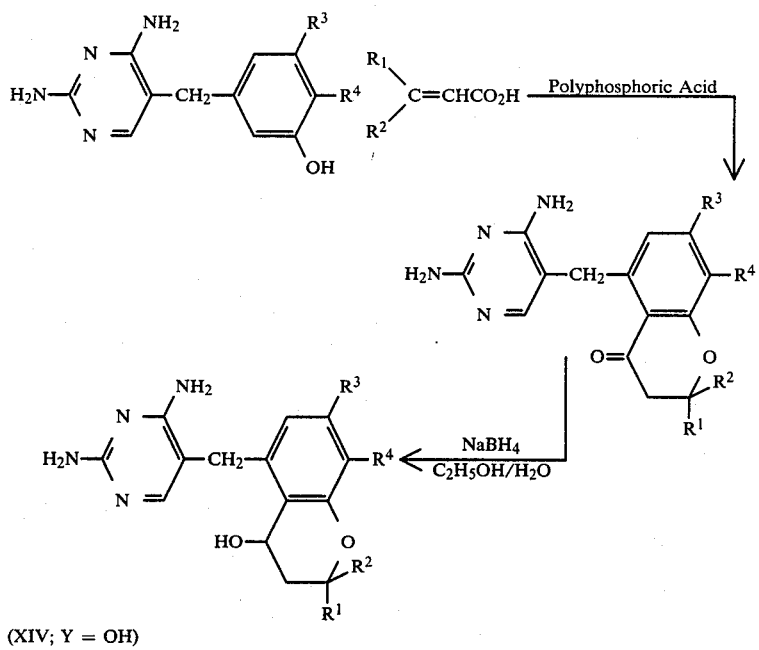

(XIV; Y = OH)

The reaction scheme is exemplified in the examples. Compounds of the formula (XIV) wherein Y is other than hydroxy may be prepared from the corresponding compound of the formula (XIV) wherein Y is hydroxy by conventional methods.

The cyclisation of a compound of the formula (XV) will take place under conventional conditions, for example those described by Harfenist, J. Org. Chem., 37, (1972), 841 or Bohlmann, Liebigs Ann. Chem., 1980, 185. It has been found that this reaction may conveniently be carried out in a high boiling, solvating solvent, i.e. a solvent having a boiling point between 100° and 300° C. and conveniently between 200° and 300° C. The reaction is conveniently carried out under an inert atmosphere such as nitrogen. This reaction may also be used to prepare bicyclic ring systems to give intermediates useful for the preparation of compounds of the formula (I).

The compounds of the formula (XV) may be prepared by conventional methods, for example by the reaction of the appropriate phenol with a halogenated alkyne in the presence of base in a solvating, polar solvent, such as a dipolar aprotic solvent. The reaction will conveniently be carried out between 0° and 50° C., and preferably between 20° and 35° C.

The reaction of a compound of the formula (XVI) with 2,4-diamino-5-hydroxymethyl pyrimidine will normally be carried out under the reaction conditions described in U.K. Pat. No. 1413471. Thus the reaction will conveniently be carried out in a polar non-phenolic solvent capable of dissolving both reactants at a non-extreme temperature, for example between 50° C. and 150° C. The reaction is preferably carried out in the presence of a strong acid catalyst, such as hydrochloric, acetic, methane sulphonic or toluene-p-sulphonic acids.

It will be apparent to those skilled in the art when certain ring substituents are present in the final compounds of the formula (I) or when

represents an unsaturated ring system, certain methods of preparation will preferably not be used to make these compounds due to the possibility of the reaction conditions changing the final product group, for example hydrogenolysis or addition across the double bond when a double bond is present.

The intermediates of the formula (VIII) to (XI), (XIV) and (XV) are novel and as such form a further aspect of the present invention.

In yet another aspect, the present invention provides the first use of the compounds of the formula (I) in human and veterinary medicine. The preferred human use of the compounds of the formula (I) is in the treatment or prophylaxis of bacterial infections.

The following examples illustrate the preparation of the compounds of the present invention and their pharmacological properties. All temperatures are in degrees centigrade.

Pharmacological data

The compounds of the present invention were subjected to standard tests in order to determine the minimum inhibitory concentration in $\mu g/ml$ needed to inhibit a range of bacterial microorganisms in-vitro.

| | Compound |
|---|---|
| TMP | 2,4-Diamino-5-(3,4,5-trimethoxybenzyl)pyrimidine |
| 1 | 2,4-Diamino-5-(7,8-dimethoxy-2$\underline{H}$—1-benzopyran-5-ylmethyl)- |

| | Compound |
|---|---|
| | pyrimidine |
| 2 | 2,4-Diamino-5-(3,4-dihydro-7,8-dimethoxy-2H—1-benzopyran-5-yl)pyrimidine |
| 3 | 2,4-Diamino-5-(8-methoxy-5-quinolylmethyl)pyrimidine |
| 4 | 2,4-Diamino-5-(7,8-dimethoxy-2-methyl-2H—1-benzopyran-5-ylmethyl)pyrimidine lactate |
| 5 | 2,4-Diamino-5-(8-amino-7-methyl-5-quinolylmethyl)-pyrimidine hydrochloride |
| 6 | 2,4-Diamino-5-(7,8-dimethoxy-2,2-dimethyl-2H—1-benzopyran-5-ylmethyl)-pyrimidine lactate |
| 7 | 2,4-Diamino-5-(7,8-dimethoxy-2-oxo-2H—1-benzopyran-5-ylmethyl)pyrimidin |
| 8 | 2,4-Diamino-5-(8-amino-7-methoxy-5-quinolylmethyl)-pyrimidine dihydrochloride |
| 9 | 2,4-Diamino-5-(8-dimethylamino-7-methyl-5-quinolylmethyl)pyrimidine dihydrochloride |
| 10 | 2,4-Diamino-5-(7,8-dimethoxy-4H—1-benzopyran-5-ylmethyl)pyrimidine acetate |
| 11 | 5-(7-Allyl-8-hydroxy-5-quinolylmethyl)-2,4-diaminopyrimidine |
| 12 | 5-(7-Allyl-8-methoxy-5-quinolylmethyl)-2,4-diaminopyrimidine |
| 13 | 5-(7-Allyl-8-hydroxy-2-methyl-5-quinolylmethyl)-2,4-diaminopyrimidine |
| 14 | 2,4-Diamino-5-(8-methoxy-7-(1-propenyl)-5-quinolylmethyl)pyrimidine |
| 15 | 2,4-Diamino-5-(8-dimethylamino-7-methoxy-5-quinolylmethyl)pyrimidine dihydrochloride |
| 16 | 5-(7-Allyl-8-methoxy-2-methyl-5-quinolylmethyl)-2,4-diaminopyrimidine |
| 17 | 2,4-Diamino-5-(7-methyl-5-quinolylmethyl)-pyrimidine dihydrochloride |
| 18 | 2,4-Diamino-5-(8-(1-pyrrolyl)-7-methyl-5-quinolylmethyl)pyrimidine acetate |
| 19 | 2,4-Diamino-5-(7,8-dimethoxy-2-methyl-4H—1-benzopyran-5-ylmethyl)-pyrimidine |
| 20 | 2,4-Diamino-5-(8-methoxy-7-propyl-5-quinolylmethyl)-pyrimidine |
| 21 | 2,4-Diamino-5-(3,4-dihydro-2-hydroxy-7,8-dimethoxy-2-methyl-2H—benzopyran-5-ylmethyl)pyrimidine in admixture with another compound |
| 22 | 2,4-Diamino-5-(7,8-dimethoxy-3,4-dihydro-2-methyl-2H—1-benzopyran-5-ylmethyl)pyrimidine |
| 23 | 2,4-Diamino-5-(8-hydroxy-7-methoxy-5-quinolylmethyl)pyrimidine |
| 24 | 2,4-Diamino-5-(7,8-dimethoxy-5-quinolylmethyl)pyrimidine |
| 25 | 2,4-Diamino-5-(8-amino-7-methoxy-5-isoquinolylmethyl)pyrimidine dihydrochloride |
| 26 | 2,4-Diamino-5-(8-amino-7-ethoxy-5-quinolylmethyl)pyrimidine |
| 27 | 2,4-Diamino-5-(7-allyl-8-(2-methoxyethoxy)-5-quinolylmethyl)pyrimidine |
| 28 | 2,4-Diamino-5-(8-amino-7-chloro-5-quinolylmethyl)pyrimidine dihydrochloride |
| 29 | 2,4-Diamino-5-(7-methoxy-5-quinolylmethyl)pyridimine |
| 30 | 2,4-Diamino-5-(8-amino-7-methylthio-5-quinolylmethyl)pyrimidine dihydrochloride |
| 31 | 2,4-Diamino-5-(7-methoxy-8-methylthio-5-quinolylmethyl)pyrimidine |
| 32 | 2,4-Diamino-5-(7-methoxy-8-nitro-5-quinolylmethyl)pyrimidine |
| 33 | 2,4-Diamino-5-(7,8-dimethoxy-2H—1-benzopyran-5-ylmethyl)pyrimidine-1-oxide |
| 34 | 2,4-Diamino-5-(5-amino-6-methyl-8-quinolylmethyl)pyrimidine |
| 35 | 2,4-Diamino-5-(5-amino-6-methoxy-8-quinolylmethyl)pyrimidine |
| 36 | 5-(7-allyl-8-methoxy-5-(1,2,3,4-tetrahydro-quinolylmethyl))-2,4-diaminopyrimidine |

Example of veterinary formulation
2,4-Diamino-5-(7,8-dimethoxy-2H-1-benzopyran-5-ylmethyl)pyrimidine Syringes for intra-mammary injection into cows were prepared from the following ingredients:
2,4-diamino-5-(7,8-dimethoxy-2H-1-benzopyran-5-ylmethyl)pyrimidine: 3.75% w/w
sulphadiazine: 7.50% w/w
glyceryl monostearate: 9.5% w/w
Tween 65: 0.5% w/w
arachis oil: 78.75% w/w The glyceryl monostearate, Tween 65 and the arachis oil were mixed together and melted at 65° C. The active ingredients (sulphadiazine and 2,4-diamino-5-(7,8-dimethoxy-2H-1-benzopyran-5-ylmethyl)pyrimidine) were stirred in and the mixture homogenised using a high speed stirrer. The resultant mixture was cooled to 50° C. and was filled into intra-mammary syringes using a 4 g fill ±5%. The manufacture and filling were carried out under sterile conditions.

EXAMPLE 1

A.

2,4-Diamino-5-(3-(3,3-diethoxypropoxy)-4,5-dimethoxybenzyl)pyrimidine

To a solution of 27.6 g, (0.1 mole) of 2,4-diamino-5-(3-hydroxy-4,5-dimethoxybenzyl)pyrimidine (D. E. Schwartz, W. Vetter, and G. Englert, *Arzneim.-Forsch.* (Drug Res.) 1970, 20, 1867; G. Rey-Bellet and R. Reiner, *Helv. Chim. Acta* 1970, 53, 945) in 400 mL of dry dimethyl sulfoxide was added 11.22 g (0.10 mole) of potassium t-butoxide. To the resulting suspension was added dropwise 17.92 g (0.107 mole) of β-chloropropionaldehyde diethylacetal. The mixture was heated at 65° overnight. The solvent was removed under vacuum and the residue was partitioned between 750 mL methylene chloride and 750 mL of 0.1N sodium hydroxide. The organic layer was separated and the aqueous layer was extracted with an additional 750 mL of methylene chloride. The organic layers were combined, washed with 750 mL of water, dried (MgSO$_4$), and purified by flash column chromatography to yield 33.38 g (83%) of the title compound (mp 105°–106.5°). Anal. Calcd for C$_{20}$H$_{30}$N$_4$O$_5$: C, 59.10; H, 7.44; N, 13.78. Found: C, 58.71; H, 7.40; N, 13.58.

B.
5-(2,4-Diamino-5-pyrimidinylmethyl)-3,4-dihydro-7,8-dimethoxy-2H-1-benzopyran-4-ol hydrochloride To a stirred suspension of finely ground product of Example 1A (6.00 g, 0.015 mole) in 100 mL of water was added 44 mL of 1N hydrochloric acid in one portion. After 17 hr at room temperature, the precipitated solid was collected on a filter, and washed with water and cold 95% ethanol, which yielded 4.72 g (83%) of the title compound (mp 165°–168°). Anal. Calcd for C$_{16}$H$_{20}$N$_4$O$_4$.HCl.H$_2$O: C, 49.68; H, 5.99; Cl, 9.16; N, 14.48. Found: C, 49.71; H, 6.01; Cl, 9.27; N, 14.33.

C.
2,4-Diamino-5-(7,8-dimethoxy-2H-1-benzopyran-5-ylmethyl)pyrimidine

A mixture of 5.00 g (0.013 mole) of the product of Example 1B and isopropyl alcohol (500 mL) was brought to reflux and then concentrated hydrochloric acid (5.0 mL) was added. The resulting clear solution was refluxed for 2 min and then cooled quickly and diluted with diethyl ether (1.5 L). The resulting white precipitate was filtered off and slurried in H$_2$O (100 mL)-concentrated ammonium hydroxide (2 mL). The white solid was filtered, washed with water and dried to give the title compound (3.18 g, 78%); purity was confirmed by $^1$H-NMR and TLC. Recrystallization of such a sample from 95% ethanol gave a white solid (mp 232°–234° dec.). Anal. Calcd for C$_{16}$H$_{18}$N$_4$O$_3$: C, 61.14; H, 5.77; N, 17.82. Found: C, 61.42; H, 5.95; N, 17.92.

EXAMPLE 2

A.
2,4-Diamino-5-(3,4-dihydro-7,8-dimethoxy-2H-1-benzopyran-5-ylmethyl)pyrimidine A solution of 0.40 g (0.0013 mole) of the product of Example 1C in 125 mL of 95% ethanol with 3 mL of glacial acetic acid and 0.03 g of platinum oxide was shaken under hydrogen (44 psi) for 16 hr. The catalyst was removed and the solvent was evaporated. The residue was partitioned between 30 mL of 0.3N sodium hydroxide and 3×30 mL of methylene chloride. The organic layers were combined and concentrated to a solid 0.29 g (72%). One recrystallization from 95% ethanol gave 0.19 g of the title compound (mp 254°–255° dec.). Anal. Calcd for C$_{16}$H$_{20}$N$_4$O$_3$: C, 60.74; H, 6.37; N, 17.71. Found: C, 60.78; H, 6.59; N, 17.38.

B.
2,4-Diamino-5-(3,4-dihydro-7,8-dimethoxy-2-methyl-2H-1-benzopyran-5-ylmethyl)pyrimidine The title compound was prepared in 80% yield from 2,4-diamino-5-(7,8-dimethoxy-2-methyl-2H-1-benzopyran-5-ylmethyl)pyrimidine by the procedure of Example 2A as white crystals, recrystallized from ethanol-water, mp 239°–240°. Anal. Calcd for C$_{17}$H$_{22}$N$_4$O$_3$: C, 61.80; H, 6.71; N, 16.96. Found: C, 61.92; H, 6.76; N, 16.88.

EXAMPLE 3

A. 8-Methoxyquinoline-5-carboxaldehyde

To a solution of 0.76 g (4.39 mmol) of 8-hydroxyquinoline-5-carboxaldehyde (G. R. Clemo and R. Howe, *J. Chem. Soc.*, 1955, 3522) in 5 mL of dimethyl sulfoxide was added 0.24 g (4.4 mmol) of sodium methoxide, while keeping the mixture under nitrogen. After stirring for 5 min, 0.56 g (4.4 mmol) of dimethyl sulfate was added. The reaction was stirred for 1 hr and the solvent removed under vacuum. The residue was partitioned between dichloromethane (100 mL) and 0.5N sodium hydroxide (50 mL); the organic layer was washed with water (100 mL), dried over anhydrous magnesium sulfate, and concentrated to give 0.61 g (74%) of 8-methoxyquinoline-5-carboxaldehyde, mp 121°–122° after recrystallization from ethanol-hexane (2:25). Anal. Calcd for C$_{11}$H$_9$NO$_2$: C, 70.58; H, 4.85; N, 7.48. Found: C, 70.55; H, 4.91; N, 7.44.

B.
3-Anilino-2-(8-methoxy-5-quinolylmethyl)acrylonitrile

The product of Example 3A (0.71 g, 3.79 mmol) was dissolved in 2 mL of dimethyl sulfoxide along with 0.61 g of 3-anilino-propionitrile. A 0.21 g (3.89 mmol) portion of sodium methoxide was added to this solution, which was then heated at 130° for 15 min, followed by cooling and dilution with an 8:1 mixture of water-ethanol. The resultant solid was separated, extracted with boiling ethyl acetate and again isolated; weight, 0.28 g, 23% of 3-anilino-2-(8-methoxy-5-quinolylmethyl)acrylonitrile. An additional 0.26 g (22%) was obtained from the filtrate by chromatography on silica gel.

C.
2,4-Diamino-5-(8-methoxy-5-quinolylmethyl)pyrimidine dihydrochloride

To 10 mL of an ethanolic guanidine solution prepared from 0.20 g (2.1 mmol) of guanidine hydrochloride and 0.12 g (2.2 mmol) of sodium methoxide was added 0.52 g (1.65 mmol) of 3-anilino-2-(8-methoxy-5-quinolylmethyl)acrylonitrile. The solution was heated under reflux for 0.5 hr, and then 5 mL of 2-methoxyethanol was added. The internal temperature was allowed to gradually increase to 120° by distillation of ethanol, after which it was heated at this temperature for 1.5 hr. The hot mixture was then filtered, and the precipitate (0.19 g, 41% of crude product) recrystallized from 95% ethanol in the presence of hydrochloric acid, giving the dihydrochloride of 2,4-diamino-5-(8-methoxy-5-quinolylmethyl)pyrimidine, 0.19 g, mp 252°–255° dec. Anal. Calcd for C$_{15}$H$_{15}$N$_5$O.2 HCl.1.5H$_2$O: C, 47.26; H, 5.29; N, 18.37; Cl, 18.60. Found: C, 47.19; H, 5.33; N, 18.35; Cl, 18.58.

EXAMPLE 4

A.
4-Amino-2-[2-(tert)-butoxycarbonylamino)acetamido]-5-(7,8-dimethoxy-2H-1-benzopyran-5-ylmethyl)pyrimidine The product of Example 1C (2.10 g, 6.68 mmol), N-tert-butoxycarbonylglycine-p-nitrophenolate (1.98 g, 6.68 mmol) and triethylamine (0.676 g, 6.68 mmol) in chloroform (100 mL) were refluxed 3 hr. The resulting mixture was adsorbed on a silica gel column and title compound eluted with 5% methanol-ethyl acetate as a white powder, after recrystallization from ethyl acetate (1.59 g, 50%); mp 206°–208° dec; structure confirmed by $^1$H-NMR. Anal. Calcd for $C_{23}H_{29}N_5O_6$: C, 58.59; H, 6.20; N, 14.85. Found: C, 58.66; H, 6.25; N, 14.42.

B.

4-Amino-5-(7,8-dimethoxy-2H-1-benzopyran-5-ylmethyl)-2-glycinamidopyrimidine dihydrochloride The product of Example 4A (0.408 g, 0.892 mmole) and isopropyl alcohol (25 mL) were heated (steam bath) while concentrated hydrochloric acid (0.40 mL) was added. The resulting clear solution was refluxed for 30 min and then cooled. The title compound was filtered off as white solid (0.271 g, 65%); mp >230° dec; structure confirmed by $^1$H-NMR. Anal. Calcd for $C_{18}H_{21}N_5O_4.2HCl.7/5H_2O$: C, 46.04; H, 5.54; N, 14.92; Cl, 15.10. Found: C, 46.69; H, 5.34; N, 14.63; Cl, 14.75.

EXAMPLE 5

A.

2,4-Diamino-5-(7,8-dimethoxy-2H-1-benzopyran-5-ylmethyl)pyrimidine lactate

A mixture of 3.00 g (9.54 mmol) of the product of Example 1C and lactic acid (1.11 g, 10.5 mmol as 85%) was dissolved in a minimum of boiling water. On cooling, white crystals of the lactate salt deposited (2.50 g, 65%), mp 195°–196.5°. Anal. Calcd for $C_{16}H_{18}N_4O_3.C_3H_6O_3$: C, 56.43; H, 5.98; N, 13.85. Found: C, 56.43; H, 5.99; N, 13.82.

B.

2,4-Diamino-5-(7,8-dimethoxy-2H-1-benzopyran-5-ylmethyl)pyrimidine Maleate

To 2,4-diamino-5-(7,8-dimethoxy-2H-1-benzopyran-5-ylmethyl)pyrimidine (3.90 g, 12.4 mmol) in 200 mL of boiling water was added a solution of maleic acid, prepared by dissolution of maleic anhydride (1.25 g, 12.7 mmol) in 50 mL of hot water. After cooling to 0° C., the crystalline salt was filtered, washed with cold water, and dried at 72° C. to give 5.07 g (94.9%) of the title compound. Anal. Calcd for $C_{20}H_{22}N_4O_7$: C, 55.81; H, 5.15; N, 13.02. Found: C, 55.78; H, 5.18; N, 12.98.

C.

2,4-Diamino-5-(7,8-dimethoxy-2H-1-benzopyran-5-ylmethyl)pyrimidine Citrate

To 2,4-diamino-5-(7,8-dimethoxy-2H-1-benzopyran-5-ylmethyl)pyrimidine (5.00 g, 15.9 mmol) in 450 mL of boiling methanol was added a solution of citric acid monohydrate (3.34 g, 15.9 mmol) in 50 mL of methanol. The solution was treated with charcoal, filtered, and evaporated to dryness. Further drying at 40° C. in a vacuum oven gave 8.01 g (99.5%) of the title compound. Karl Fisher analysis: 5.3% $H_2O$. Anal. Calcd for $C_{16}H_{18}N_4O_3.C_6H_8O_7.1.5H_2O$: C, 49.53; H, 5.48; N, 10.50. Found: C, 49.54; H, 5.49; N, 10.47.

D.

2,4-Diamino-5-(7,8-dimethoxy-2H-1-benzopyran-5-ylmethyl)pyrimidine Ascorbate

To 2,4-diamino-5-(7,8-dimethoxy-2H-1-benzopyran-5-ylmethyl)pyrimidine (5.00 g, 15.9 mmol) in 450 mL of boiling methanol was added a solution of L (+)-ascorbic acid (2.80 g, 15.9 mmol) in 50 mL of methanol. The solution was treated with charcoal, filtered, and evaporated to dryness. Further drying at 40° C. in a vacuum oven gave 7.58 g (97.2%) of the title compound. Anal. Calcd for $C_{16}H_{18}N_4O_3.C_6H_8O_6.H_2O$: C, 51.97; H, 5.55; N, 11.02. Found: C, 51.95; H, 5.57; N, 11.02.

EXAMPLE 6

A.

2,4-Diamino-5-(3,4-dihydro-7,8-dimethoxy-2-methyl-4-oxo-2H-1-benzopyran-5-ylmethyl)pyrimidine A mixture of 2,4-diamino-5-(3-hydroxy-4,5-dimethoxybenzyl)pyrimidine (2.76 g, 0.01 mole) and crotonic acid (0.87 g, 0.01 mole) in polyphosphoric acid (27 g) was stirred and heated on a steam bath for 4 hr. The reaction mixture was cooled to 50° and poured onto ice (100 g) with stirring. The resulting solution was basified to pH 8.0 with concentrated ammonium hydroxide, giving a suspension which was then extracted with methylene chloride (3×100 mL). The combined extracts were washed with 0.1N sodium hydroxide (2×100 mL), water (100 mL) and then dried over anhydrous magnesium sulfate. Evaporation of solvent in vacuo gave the title compound (1.0 g, 29%). This was recrystallised from 95% ethanol to give 2,4-diamino-5-(3,4-dihydro-7,8-dimethoxy-2-methyl-4-oxo-2H-1-benzopyran-5-ylmethyl)pyrimidine as the hemihydrate, mp 128°–132°. Anal. Calcd for $C_{17}H_{20}N_4O_4.\frac{1}{2}H_2O$: C, 57.78; H, 5.99; N, 15.85. Found: C, 57.79; H, 6.02; N, 15.86.

B.

2,4-Diamino-5-(3,4-dihydro-4-hydroxy-7,8-dimethoxy-2-methyl-2H-1-benzopyran-5-ylmethyl)pyrimidine To a suspension under nitrogen of 2,4-diamino-5-(3,4-dihydro-7,8-dimethoxy-2-methyl-4-oxo-2H-1-benzopyran-5-ylmethyl)pyrimidine hemihydrate (0.47 g, 1.4 mmol) in ethanol (10 mL) at 5° was added in one portion a solution of sodium borohydride (0.55 g, 1.45 mmol) in water (1 mL). The reaction mixture was allowed to warm to room temperature; complete solution was attained in 30 min. The solution was cooled in ice with stirring for 3 hr. The resulting precipitate of 2,4-diamino-5-(3,4-dihydro-4-hydroxy-7,8-dimethoxy-2-methyl-2H-1-benzopyran-5-ylmethyl)pyrimidine monohydrate (0.4 g, 83%) was recrystallized from 95% ethanol to give the monohydrate, mp 201°–203°. Anal. Calcd for $C_{17}H_{22}N_4O_4.H_2O$: C, 56.03; H, 6.64; N, 15.37. Found: C, 56.07; H, 6.65; N, 15.38.

C.

2,4-Diamino-5-(7,8-dimethoxy-2-methyl-2H-1-benzopyran-5-ylmethyl)pyrimidine lactate The product of Example 6B was used in the procedure of Example 1C. to give free base of the title compound, after recrystallization from ethanol, identical to that of Example 21 (30% yield). The lactate was prepared in 48% yield by the procedure of Example 5A to give to white solid, mp 183°–185° dec. Anal. Calcd for $C_{17}H_{20}N_4O_3.C_3H_6O_3$: C, 57.41; H, 6.26; N, 13.39. Found: C, 57.41; H, 6.29; N, 13.39.

EXAMPLE 7

A.

2,4-Diamino-5-(3,4-dihydro-7,8-dimethoxy-2,2-dimethyl-4-oxo-2H-1-benzopyran-5-ylmethyl)pyrimidine Following the procedure of Example 6A with 3,3-dimethylacrylic acid in place of crotonic acid, the title compound was prepared in low yield (9%). The structure was confirmed by nmr and mass spectrometry.

B.
2,4-Diamino-5-(3,4-dihydro-4-hydroxy-7,8-dimethoxy-2,2-dimethyl-2H-1-benzopyran-5-ylmethyl)pyrimidine The product of Example 7A (0.33 g, 0.92 mmol) was used in the procedure of Example 6B to give the title compound as white solid (0.15 g, 45%).

C.
2,4-Diamino-5-(7,8-dimethoxy-2,2-dimethyl-2H-1-benzopyran-5-ylmethyl)pyrimidine lactate The product of Example 7B (0.15 g, 0.40 mmol) was used in the procedure of Example 6C to give the title compound as the lactate monohydrate (0.078 g, 42%), mp 196.5°–198°. The structure was confirmed by NMR and mass spectra. Anal. Calcd for $C_{18}H_{22}N_4O_3 \cdot C_3H_6O_3 \cdot H_2O$: C, 55.99; H, 6.71; N, 12.44. Found: C, 55.89; H, 6.70; N, 12.42.

EXAMPLE 8

A.
5-(8-Amino-7-methyl-5-quinolylmethyl)-2,4(1H,3H)-pyrimidinedione

A mixture of 8.36 g (0.0406 mole) of 5-[(dimethylamino)methyl]uracil hydrochloride (B. Roth, J. Z. Strelitz, and B. S. Rauckman, J. Med. Chem. 23, 379 (1980) and 6.43 g (0.0406 mole) of 8-amino-7-methylquinoline (R. Long and K. Schofield, J. Chem. Soc. 1953, 2350) in 60 ml of ethylene glycol under nitrogen was heated at 135° for 4 hours. The mixture was cooled and the precipitated solid was collected, washed with ethanol and ether and dried. This crude product was purified by suspension in 550 ml of boiling ethanol and collection of the insoluble product. Yield, 8.90 g of the title compound (78%) m.p. 302°–305° (dec.). Anal. Calcd for $C_{21}H_{20}N_4$: C, 76.89; H, 6.14; N, 17.06. Found: C, 76.82; H, 6.17; N, 17.04.

B.
5-(8-Amino-7-methyl-5-quinolylmethyl)-2,4-dichloropyrimidine

A mixture of 2.82 g (0.01 mole) of 5-(8-amino-7-methyl-5-quinolylmethyl-2,4(1H,3H)pyrimidinedione in 50 ml of phosphoryl chloride was heated at reflux for 3.5 hours. The excess POCl₃ was removed in vacuo and the residue was stirred with aqueous sodium carbonate. The resulting solid was dried to give 2.66 g (83%) of title compound.

A portion was recrystallized from ethanol to give an analytical sample, m.p. 209°–211°. Anal. Calcd for $C_{15}H_{12}N_4Cl_2$: C, 56.44; H, 3.79; N, 17.55; Cl, 22.21. Found: C, 56.27; H, 4.09; N, 17.46; Cl, 22.11.

C.
2,4-Diamino-5-(8-amino-7-methyl-5-quinolylmethyl)-pyrimidine dihydrochloride

A suspension of 2.00 g (6.26 mmole) of 5-(8-amino-7-methyl-5-quinolylmethyl-2,4-dichloropyrimidine in 40 ml of ethanol saturated with ammonia was heated in an autoclave at 150° for 9 hours. Solids that precipitated on cooling were washed with water and dried to give 1.28 g of crude product (73%) as the free base.

A portion was converted to the dihydrochloride hydrate by recrystallization from 60% aqueous ethanol with concentrated hydrochloric acid, m.p. >310° dec. Anal. Calcd for $C_{15}H_{16}N_6 \cdot 2HCl \cdot H_2O$: C, 48.52; H, 5.43; N, 22.64; Cl, 19.10. Found: C, 48.52; H, 5.45; N, 22.62; Cl, 19.06.

EXAMPLE 9

2,4-Diamino-5-(7,8-dimethoxy-2-oxo-2H-1-benzopyran-5-ylmethyl)pyrimidine

A mixture of 1.38 g (0.005 mole) of 2,4-diamino-5-(3-hydroxy-4,5-dimethoxybenzyl)pyrimidine and 1.01 g (0.0075 mole) of L-(−)-malic acid in polyphosphoric acid (30 g) was heated at 90°–100° for 4 hours. The resulting clear syrup was poured into ice-water (150 mL) and basified (pH 8) with conc'd ammonium hydroxide. The title compound was filtered off and washed with ethanol. Yield, 0.26 g (16%); m.p. 278°–280° dec; structure confirmed by $^{13}C$ and $^1H$ NMR and mass spectra. Anal. Calcd. for $C_{16}H_{18}N_4O_3$: C, 58.53; H, 4.91; N, 17.07. Found: C, 58.27; H, 4.99; N, 16.97.

EXAMPLE 10

2,4-Diamino-5-(7,8-dimethoxy-2-methyl-4H-1-benzopyran-5-ylmethyl)pyrimidine

A solution of 2,4-diamino-5-(7,8-dimethoxy-2-methyl-2H-1-benzopyran-5-ylmethyl)pyrimidine (967 mg, 2.94 mmol) and potassium t-butoxide (991 mg, 8.83 mmol) in dimethyl sulfoxide was maintained at 60°–70° for 0.5 hr under nitrogen. The solution was cooled and diluted with water (50 mL). The resulting precipitate (920 mg) was recrystallized from 95% ethanol to give the title compound as white crystals (820 mg, 85%), mp 215°–217° dec., structure confirmed by NMR spectrum. Anal. Calcd for $C_{17}H_{20}N_4O_3$: C, 62.18; H, 6.14; N, 17.06. Found: C, 61.95; H, 6.20; N, 17.00.

EXAMPLE 11

A.
5-(7-Allyl-8-hydroxy-5-quinolylmethyl)-2,4-diaminopyrimidine

7-Allyl-8-hydroxyquinoline [H. Fiedler, Arch. Pharm., 297, 108 (1964)] (33.0 g, 0.227 mol), 2,4-diamino-5-hydroxymethylpyrimidine (32.7 g, 0.227 mole), glacial acetic acid (300 mL) and concentrated HCl (31.5 mL) were refluxed for 5 hr. The resulting precipitate was filtered off and then slurried with $H_2O$ (250 mL) and sufficient $NH_4OH$ to give a pH of 8. The dissolved solid was filtered off, washed with $H_2O$ and dried to give the title compound as yellow powder (19.7 g, 28%), mp 229°–231° dec., structure confirmed by NMR. Anal. Calcd for $C_{17}H_{17}N_5O$: C, 66.43; H, 5.58; N, 22.79. Found: C, 66.41; H, 5.59; N, 22.78. Additional product (5.0 g, 7%) was obtained by evaporation of filtrates and chromatography to separate unreacted starting materials.

B.
5-(7-Allyl-8-methoxy-5-quinolylmethyl)-2,4-diaminopyrimidine

A solution of the product of Example 11A (5.00 g, 16.3 mmol), potassium-t-butoxide (1.83 g) and methyl iodide (2.31 g) in dimethyl sulfoxide (25 mL) was stirred for 0.5 hr and then diluted with $H_2O$ (100 mL). The tan precipitate (4.1 g) was chromatographed on silica gel. Elution with 10–15% methanol-methylene chloride gave the title compound as white powder (3.25 g, 62%), mp 227°–228°. Anal. Calcd for $C_{18}H_{19}N_5O$: C, 67.27; H, 5.96; N, 21.79. Found: C, 67.21; H, 6.00; N, 21.75.

C. 2,4-Diamino-5-(8-methoxy-7-(1-propenyl)-5-quinolylmethyl)pyrimidine

A solution of the product from Example 11B (1.85 g, 5.76 mmol) and potassium t-butoxide (65 mg) in dimethyl sulfoxide (10 mL) was heated at 80°–90° for 0.5 hr. The solution was diluted with $H_2O$ (25 mL), cooled and the precipitate filtered and washed with $H_2O$. Crystallization from 95% ethanol gave the title compound as off-white needles (1.40 g, 76%), mp 260°–262° dec., structure confirmed by NMR. Anal. Calcd for $C_{18}H_{19}N_5O \cdot \frac{1}{4}H_2O$: C, 66.34; H, 6.03; N, 21.49. Found: C, 66.26; H, 6.06, N, 21.42.

EXAMPLE 12

A. 5-(7-Allyl-8-hydroxy-2-methyl-5-quinolylmethyl)-2,4-diaminopyrimidine

7-Allyl-8-hydroxy-2-methylquinoline [prepared as 7-allyl-8-hydroxyquinoline Example 11A] was converted to the title compound in 61% yield by the procedure of Example 11A; white powder from 95% ethanol, mp 236°–237°. Anal. Calcd for $C_{18}H_{19}N_5O$: C, 67.27; H, 5.96; N, 21.79. Found: C, 67.39; H, 5.97; N, 21.80.

B. 5-(7-Allyl-8-methoxy-2-methyl-5-quinolylmethyl)-2,4-diaminopyrimidine 5-(7-allyl-8-hydroxy-2-methyl-5-quinolylmethyl)-2,4-diaminopyrimidine was methylated to the title compound by the procedure of example 11B in 80% yeild; white powder from ethanol, mp 219°–222°. Anal. Calcd for $C_{19}H_{21}N_5O$: C, 68.04; H, 6.31; N, 20.88. Found: C, 67.97; H, 6.34; N, 20.83.

EXAMPLE 13

A. 7-Methoxy-8-nitroquinoline

To a freshly prepared solution of sodium (16.5 g, 0.720 mol) in methanol (750 mL) was added 7-chloro-8-nitroquinoline (18.72 g, 0.090 mol) [E. Fourneau, M. and Mme. Tréfouel, and A. Wancolle, *Bull. Soc. Chim. Fr.*, 47, 738(1930); A. K. Sen, N. K. Ray, V. P. Basu, *J. Sci. Ind. Res.*, 11B, 322(1952) (C.A. 47, 4339e)]. This mixture was refluxed for 3 hr, cooled, then filtered to collect the precipitated solid. This solid was slurried in water, collected on a filter and dried; yield, after recrystalllization from toluene, 16.12 g (88%); mp 178°–178.5°: Anal. Calcd for $C_{10}H_8N_2O_3$: C, 58.82; H, 3.95; N, 13.72. Found: C, 58.66; H, 3.87; N, 13.69.

B. 8-Amino-7-methoxyquinoline

A suspension of the product from Example 13A (4.83 g, 2.36 mmol) in ethanol (100 mL) with 10% palladium on carbon (0.10 g) was hydrogenated at 40 psi until the uptake of hydrogen ceased. The reaction was warmed to dissolve precipitated solids, filtered to remove the catalyst, then concentrated to a small volume where upon the title compound separated (3.40 g, 82%); mp 114°–115°. Anal. Calcd for $C_{10}H_{10}N_2O$: C, 68.95; H, 5.79; N, 16.08. Found: C, 68.94; H, 5.80; N, 16.01.

C. 5-(8-Amino-7-methoxy-5-quinolylmethyl)-2,4-(1$\underline{H}$,3$\underline{H}$)pyridimidinedione Following the procedure of Example 8A with the product from Example 13B (7.31 g, 41.9 mmol), the title compound was prepared (10.07 g, 80%) mp >320° dec. Anal. Calcd for $C_{15}H_{14}N_4O_3$: C, 60.40; H, 4.73; N, 18.78. Found: C, 60.17; H, 4.76; N, 18.41.

D. 5-(8-Amino-7-methoxy-5-quinolylmethyl)-2,4-dichloropyrimidine

The product of Example 13C (3.00 g, 10.0 mmol) was used in the procedure of Example 8B to give the title compound (2.49 g, 74%), mp 149°–151° dec. Anal. Calcd for $C_{15}H_{12}N_4Cl_2O$: C, 53.75; H, 3.61; N, 16.71; Cl, 21.15. Found: C, 53.76; H, 3.63; N, 16.71; Cl, 21.09.

E. 2,4-Diamino-5-(8-amino-7-methoxy-5-quinolylmethyl)pyrimidine dihydrochloride The product of Example 13D (2.49 g, 7.4 mmol) was used in the procedure of Example 8C to give the title compound (1.67 g, 61%), mp 287°–289° dec. Anal. Calcd for $C_{15}H_{16}N_6O \cdot 2HCl$: C, 48.79; H, 4.91; N, 22.76; Cl, 19.20. Found: C, 48.65; H, 4.94; N, 22.72; Cl, 19.13.

EXAMPLE 14

A. 5-(8-Dimethylamino-7-methoxy-5-quinolylmethyl)-2,4-(1$\underline{H}$,3$\underline{H}$)pyrimidinedione To a solution of 5-(8-amino-7-methoxy-5-quinolylmethyl)-2,4-(1$\underline{H}$,3$\underline{H}$)pyrimidinedione (3.10 g, 10.0 mmol) in 88% formic acid (40 mL) was added 37% formaldehyde (2.5 g). After refluxing 18 hr, the solution was evaporated to a red glass which was dissolved in water (20 mL). Neutralization of this solution with $NaHCO_3$ gave a tan precipitate (3.1 g). Recrystallization from 95% ethanol gave the title compound as yellow needles (1.2 g, 60%), mp 260°–263° dec. Anal. Calcd for $C_{17}H_{18}N_4O_3$: C, 62.56; H, 5.56; N, 17.17. Found: C, 62.54; H, 5.56; N, 17.17.

B. 2,4-Diamino-5-(8-dimethylamino-7-methoxy-5-quinolylmethyl)pyrimidine dihydrochloride The product of Example 16A (1.30 g, 3.98 mmol) was converted to the 2,4-dichloropyrimidine by the method of Example 8B. Amination by the procedure of Example 8C gave 2,4-diamino-5-(8-dimethylamino-7-methoxy-5-quinolylmethoxy)pyrimidine dihydrochloride (20%), recrystallized from 95% ethanol, mp 242°–244° dec. Anal. Calcd for $C_{17}H_{20}N_6O \cdot 2HCl$: C, 51.39; H, 5.58; N, 21.15, Cl, 17.85. Found: C, 51.39; H, 5.60; N, 21.12; Cl, 17.80.

EXAMPLE 15

A. 5-(8-(1-Pyrrolyl)-7-methyl-5-quinolylmethyl)-2,4-(1$\underline{H}$,3$\underline{H}$)pyrimidine dione A mixture of the product of Example 8A (5.00 g, 17.7 mmol) and 95% 2,5-dimethoxytetrahydrofuran (2.71 g, 19.5 mmol) in glacial acetic acid (50 mL) was heated at reflux for 30 min, then cooled. The solvent was evaporated and the residue was stirred with water. The solid that separated was collected and triturated with boiling ethanol to give the title compound as a green solid (3.73 g, 63%) which was suitable for further transformation. The structure was confirmed by NMR.

B.
2,4-Diamino-5-(8-(1-pyrrolyl)-7-methyl-5-quinolylmethyl)pyrimidine acetate The product of Example 15A (3.73 g, 11.2 mmol) was used in the procedure of Example 8B to give 2,4-dichloro-5-(8-(1-pyrrolyl)-7-methyl-5-quinolylmethyl)-pyrimidine (1.63 g, 39%). A portion of this (1.44 g, 3.90 mmol) was used without further purification in the procedure of Example 8C to give the free base of the title compound (1.08 g, 84%). The acetate salt was obtained by lyophilizing a solution of the free base in acetic acid-water. The structure was confirmed by NMR and mass spectrometry; mp-shrinks to a glass at 110°. Anal. Calcd for $C_{19}H_{18}N_6 \cdot C_2H_4O_2 \cdot 0.4H_2O$: C, 64.63; H, 5.78; N, 21.13. Found: C, 63.35; H, 5.34; N, 21.15.

EXAMPLE 16

A.
5-(8-Dimethylamino-7-methyl-5-quinolylmethyl)-2,4-(1H,3H)pyrimidine dione The product of Example 8A (1.41 g, 5.0 mmol) was used in the procedure of Example 14A to give the title compound as a tan solid (0.63 g, 41%). Recrystallization from ethanol gave an analytical sample, mp 267°–270° dec. Anal. Calcd for $C_{17}H_{18}N_4O_2$: C, 65.79; H, 5.85; N, 18.05. Found: C, 65.54; H, 5.91; N, 17.98.

B.
2,4-Diamino-5-(8-dimethylamino-7-methyl-5-quinolylmethyl)pyrimidine dihydrochloride The product of Example 16A (1.33 g, 4.30 mmol) was used in the procedure of Example 8B to give 2,4-dichloro-5-(8-dimethylamino-7-methyl-5-quinolylmethyl)pyrimidine (0.79 g, 53%). This was used without further purification in the procedure of Example 8C to give the title compound as tan solid (0.32 g, 37%), mp 250°–252° dec., after crystallization 95% ethanol containing HCl. Anal. Calcd for $C_{17}H_{20}N_6 \cdot 2HCl \cdot 0.25H_2O$: C, 52.92; H, 5.88; N, 21.78; Cl, 18.38. Found: C, 52.77; H, 5.90; N, 21.74; Cl, 18.22.

EXAMPLE 17

A.
2,4-Diamino-5-(8-hydroxy-7-propyl-5-quinolylmethyl)-6-methylthio pyrimidine To a cold (0°) solution of 8-hydroxy-7-propylquinoline (5.7 g, 30.4 mmol) and 26% aqueous dimethylamine (15 g, 83 mmol) in 30 mL of ethanol was added dropwise 37% aqueous formaldehyde (4.5 g, 55.4 mmol). After stirring at room temperature for 1 hr, the mixture was refluxed for 2 hr, cooled and evaporated to dryness. The residue was diluted with water, extracted twice with ether and the extracts combined and dried (MgSO$_4$). Evaporation gave 5-dimethylaminomethyl-8-hydroxy-7-propylquinoline as a syrup (7.00 g, 94%), structure confirmed by NMR. A portion of this syrup (2.44 g, 10 mmol) was heated under nitrogen with 2,4-diamino-6-methylthiopyrimidine (1.56 g, 10 mmol) in ethylene glycol (20 mL) at 120°–160° for 1 hr, then cooled. The solid that separated was collected, and washed with ether and hexanes to give the title compound (3.20 g, 90%). An analytical sample was obtained by recrystallization from 95% ethanol, mp. 204°–206° dec. Anal. Calcd for $C_{18}H_{21}N_5SO$: C, 60.82; H, 5.95; N, 19.70; S, 9.02. Found: C, 60.81; H, 5.98; N, 19.67; S, 9.02.

B.
2,4-Diamino-5-(8-methoxy-7-propyl-5-quinolylmethyl)-6-methylthio pyrimidine The product of Example 17A (2.70 g, 7.6 mmol) was used in the procedure of Example 11B to give the title compound as a white solid (2.16 g, 77%) mp 216°–218° dec., after recrystallization from 95% ethanol. Anal. Calcd for $C_{19}H_{23}N_5SO$: C, 61.76; H, 6.27; N, 18.95; S, 8.68. Found: C, 61.69; H, 6.30; N, 18.92; S, 8.65.

C.
2,4-Diamino-5-(8-methoxy-7-propylquinolylmethyl)pyrimidine

The product of Example 17B (0.86 g, 2.3 mmol) was heated at reflux with W-2 Raney nickel (10 g) in 95 % aqueous 2-methoxyethanol for 2 hr. The catalyst was removed by filtration through Celite, then washed with hot 2-methoxyethanol. The filtrate-wash was concentrated to give the title compound as white powder (0.56 g, 75%), mp 224°–228° dec., after recrystallization from 95% ethanol. Anal. Calcd for $C_{18}H_{21}N_5O$: C, 66.85; H, 6.55; N, 21.66. Found: C, 66.80; H, 6.55; N, 21.66.

Alternatively, the product of Example 11B (260 mg, 0.84 mmol) was shaken with 10% palladium on carbon in 95% ethanol (25 mL) under hydrogen (50 psi) for 2 hr. Filtration of the catalyst and concentration gave the title compound (0.25 g, 96%).

EXAMPLE 18

A. 8-Hydroxy-7-methoxyquinoline

Finely ground 7,8-dimethoxyquinoline-2-carboxylic acid (1.00 g, 4.3 mmol) (W. Ried, A. Berg and G. Schmidt, Chem. Ber., 85, 204 (1952)) was heated under nitrogen in a flask submerged in an oil bath at 185° until the evolution of gases had ceased from the melt. The reaction was cooled and 75% aqueous sulfuric acid (8.1 mL) was carefully added. The resulting solution was heated at 105°–125° for 2 hr, cooled, poured over ice and taken to pH 5 with 5N sodium hydroxide. The mixture was filtered, and the filtrate was extracted with methylene chloride (4×50 mL). The extracts were dried (MgSO$_4$) and concentrated in vacuo to give 8-hydroxy-7-methoxyquinoline (0.40 g, 53%), mp 113°–115° after recrystallization from 95% ethanol. Anal. Calcd for $C_{10}H_9NO_2$: C, 68.56; H, 5.18; N, 8.00. Found: C, 68.33; H, 5.17; N, 7.97.

B.
2,4-Diamino-5-(8-hydroxy-7-methoxy-5-quinolylmethyl)pyrimidine

The product of Example 18A (1.00 g, 5.7 mmol) was used in the procedure of Example 11A to give 2,4-diamino-5-(b 8-hydroxy-7-methoxy-5-quinolylmethyl)-pyrimidine (0.18 g, 11%), mp 243°–245° dec., after recrystallization from 95% ethanol. Anal. Calcd for $C_{15}H_{15}N_5O_2 \cdot 0.5H_2O$: C, 58.82; H, 5.26; N, 22.86. Found: C, 58.73; H, 5.30; N, 22.79. The structure was confirmed by NMR and mass spectrometry.

C.
2,4-Diamino-5-(7,8-dimethoxy-5-quinolylmethyl)pyrimidine

The product of Example 18B was used in the procedure of Example 11B to give the title compound (55%), mp 257°-259° dec., after recrystallization from 95% ethanol. The structure was confirmed by NMR and mass spectrometry. Anal. Calcd for $C_{16}H_{17}N_5O_2.0.25$-$H_2O$: C, 60.84; H, 5.58; N, 22.17. Found: C, 60.92; H, 5.50; N, 22.13.

EXAMPLE 19

A. 5-(7-Methyl-5-quinolylmethyl)-2,4-(1H,3H)pyrimidinedione

The product from Example 8A (1.41 g, 5.0 mmol) was dissolved in 50% aqueous sulfuric acid (10.5 mL) with heating, then cooled to 5° to form a suspension. A solution of sodium nitrite (0.36 g, 5.0 mmol) in water (3.5 mL) was added, keeping the temperature below 10°. After the addition was complete, cold 50% hypophosphorus acid (3.3 mL) was added in one portion. The mixture was slowly allowed to warm to room temperature over 2 hr, and additional 50% hypophosphorus acid (3.3 mL) was added. After 5 days, the mixture was diluted with water, heated to dissolve the solids and carefully taken to pH 8 with solid sodium carbonate. The title compound separated on cooling (1.25 g, 95%), mp 293°-296° dec., after recrystallization from ethanol. Anal. Calcd for $C_{15}H_{13}N_3O_2.0.5H_2O$: C, 65.21; H, 5.11; N, 15.21. Found: C, 65.03; H, 5.29; N, 15.23.

B. 2,4-Diamino-5-(7-methyl-5-quinolylmethyl)pyrimidine dihydrochloride

The product of Example 19A (0.51 g, 1.9 mmol) was used in the procedure of Example 8B to give 2,4-dichloro-5-(7-methyl-5-quinolylmethyl)pyrimidine (0.52 g, 90%). This was used without further purification in the procedure of Example 8C to give the title compound as a pink solid, mp 338°-340° dec. Anal. Calcd for $C_{15}H_{15}N_5.2HCl.H_2O$: C, 50.57; H, 5.38; N, 19.66; Cl, 19.90. Found. C, 50.40; H, 5.42; N, 19.59; Cl, 19.83.

EXAMPLE 20

(Alternative to procedure of Example 6)

A. 2,4-Diamino-5-[3,4-dimethoxy-5-(1-methoxy-2-propynyloxy)benzyl]pyrimidine The title compound was prepared in 62% yield from 2,4-diamino-5L -(3-hydroxy-4,5-dimethoxybenzyl)pyrimidine and 3-chloro-1-butyne by the procedure of Example 1A. Crystallization from methanol gave white solid; mp 153°-155°. Anal. Calcd for $C_{17}H_{20}N_4O_3$: C, 62.18; H, 6.14; N, 17.06. Found: C, 61.93; H, 6.22; N, 16.98.

B. 2,4-Diamino-5-(7,8-dimethoxy-2-methyl-2H-1-benzopyran-5-ylmethyl)pyrimidine A solution of 2,4-diamino-5-[3,4-dimethoxy-5-(1-methyl-2-propynyloxy)benzyl]pyrimidine (4.28 g, 13.0 mmol) in N,N-diethylaniline (200 mL) was refluxed under nitrogen for 0.5 hr. The hot solution was filtered to remove dark tarry material. The filtrate was cooled and diluted with hexanes (200 mL). The precipitate (3.8 g) was recrystallized from ethanol to give title compound as off-white powder (1.56 g, 37%); mp 219°-221° dec. Anal. Calcd for $C_{17}H_{20}N_4O_3$: C, 62.18; H, 6.14; N, 17.06. Found: C, 61.91; H, 6.20; N, 16.93.

EXAMPLE 21

(Alternative to procedure of Example 1)

A. 2,4-Diamino-5-[3,4-dimethoxy-5-(2-propynyloxy)benzyl]pyrimidine

The title compound was prepared from 2,4-diamino-5-(3-hydroxy-4,5-dimethoxybenzyl)pyrimidine and propargyl chloride by the procedure of Example 1A. Recrystallization from 95% ethanol gave off-white needles (73%); mp 160°-161°. Anal. Calcd for $C_{16}H_{18}N_4O_3$: C, 61.13; H, 5.77; N, 17.82. Found: C, 60.96; H, 5.80; N, 17.75.

B. 2,4-Diamino-5-(7,8-dimethoxy-2H-1-benzopyran-5-ylmethyl)pyrimidine

The title compound was prepared in 40% yield from 2,4-diamino-5-[3,4-dimethoxy-5-(2-propynyloxy)benzyl]pyrimidine by the procedure of Example 20B. The product was identical by spectral and analytical analyses to that prepared by the procedure of Example 1.

EXAMPLE 22

A. 7-Ethoxy-8-nitroquinoline

A mixture of 7-chloro-8-nitroquinoline (3.00 g, 14.4 mmol), sodium (2.65 g) and absolute ethanol (100 mL) was refluxed for 4.5 hr and cooled. The tan precipitate was filtered off, slurried with water and dried to give title compound as tan solid (2.72 g, 87%); mp 161°-164°. Anal. Calcd for $C_{11}H_{10}N_2O_3$: C, 60.55; H, 4.62; N, 12.84. Found: C, 60.34; H, 4.68; N, 12.78.

B. 8-Amino-7-ethoxyquinoline

7-Ethoxy-8-nitroquinoline (2.62 g, 12.0 mmole), in absolute ethanol (200 mL) was shaken with 10% palladium on carbon (0.10 g) under hydrogen (50 psi) for 3 hr. The catalyst was filtered off and the filtrate concentrated to 10 mL. The title compound crystallized as yellow needles (1.86 g, 82%); mp 94°-95°. Anal. Calcd for $C_{11}H_{12}N_2O$: C, 70.19; H, 6.43; N, 14.88. Found: C, 70.16; H, 6.47; N, 14.87.

C. 5-(8-Amino-7-ethoxy-5-quinolylmethyl)-2,4-(1H,3H)pyrimidinedione

Following the procedure of Example 8A with 8-amino-7-ethoxyquinoline (1.76 g, 9.35 mmol), the title compound was prepared (1.57 g, 54%); mp >200° dec. Anal. Calcd for $C_{16}H_{16}N_4O_3$: C. 61.53; H, 5.16; N, 17.94. Found: C, 61.62; H, 5.22; N, 17.85.

D. 2,4-Diamino-5-(8-amino-7-ethoxy-5-quinolylmethyl)pyrimidine

The product of Example 22A (1.50 g, 4.80 mmol) was used in the procedure of Example 8B to give 5-(8-amino-7-ethoxy-5-quinolylmethyl)-2,4-dichloropyrimidine as yellow solid (1.51 g, 90%). This solid was used without further purification in the procedure of Example 8C to give the title compound as yellow solid (1.11 g, 75%), recrystallized from ethanol; mp 218°-220° dec. Anal. Calcd for $C_{16}H_{18}N_6O$: C, 61.92; H, 5.85; N, 27.08. Found: C, 61.68; H, 5.88; N, 26.96.

EXAMPLE 23

A. 7-Methylthio-8-nitroquinoline

A solution of sodium methylmercaptide was prepared by bubbling methyl mercaptan through a cooled (ice bath) solution of sodium (1.1 g, 48 mequiv) in methanol (200 mL). 7-Chloro-8-nitroquinoline (5.00 g, 24.0 mmol) was added and the resulting mixture stirred at room temperature for 2 days. The precipitate was filtered off, washed with methanol and water to give 7-methylthio-8-nitroquinoline as pale yellow solid (4.72 g, 89%); mp 163°–164°. Anal. Calcd for $C_{10}H_8N_2O_2S$: C, 54.33; H, 3.66; N, 12.72; S, 14.56. Found: C, 54.61; H, 3.68; N, 12.68; S, 14.48.

B. 5-(8-Amino-7-methylthio-5-quinolylmethyl)-2,4-(1$\underline{H}$,3$\underline{H}$)pyrimidinedione A stirred mixture of 7-methylthio-8-nitroquinoline (3.00 g, 13.6 mmol), water (15 mL) and glacial acetic acid (15 mL) was maintained at 110° while iron (mesh 40, 2.38 g) was added in portions over 1.25 hr. After an additional 0.5 hr, the mixture was evaporated to dryness. The residual black glass was extracted with refluxing ethyl acetate (3×100 mL). The ethyl acetate extracts were washed with 2N NaOH (50 mL), H$_2$O (50 mL), saturated NaCl (50 mL) and dried (MgSO$_4$). Evaporation left 8-amino-7-methylthioquinoline as a red syrup (2.6 g) of sufficient purity (TLC, $^1$H-NMR) for use in the procedure of Example 8A to prepare the title compound as a tan solid (2.02 g, 47%); mp 308°–310° dec; structure confirmed by $^1$H-NMR. Anal. Calcd for $C_{15}H_{14}N_4SO_2$: C, 57.31; H, 4.49; N, 17.82; S, 10.20. Found: C, 57.39; H, 4.50; N, 17.80; S, 10.15.

C. 2,4-Diamino-5-(8-amino-7-methylthio-5-quinolylmethyl)pyrimidine dihydrochloride The product of Example 23B (1.84 g, 5.85 mmol) was used in the procedure of Example 8B to give 5-(8-amino-7-methylthio-5-quinolylmethyl)-2,4-dichloropyrimidine as tan powder (1.93 g). This solid was used without further purification in the procedure of Example 8C to give the free base of the title compound as yellow powder (1.54 g), after purification on a silica gel column eluted with methanol-methylene chloride (1:4). Recrystallization from ethanol-water containing hydrochloric acid gave the title compound as red-orange needles (1.26 g, 56% from the product of Example 23B); mp >300° dec. Anal. Calcd for $C_{15}H_{16}N_6S.2HCl$: C, 46.76; H, 4.71; N, 21.81; S, 8.32; Cl, 18.40. Found: C, 46.75; H, 4.75; N, 21.78; S, 8.29; Cl, 18.35.

EXAMPLE 24

2,4-Diamino-5-(8-amino-7-chloro-5-quinolylmethyl)-pyrimidine dihydrochloride A solution of 7-chloro-8-aminoquinoline (C. C. Price and D. B. Guthrie, *J. Amer. Chem. Soc.* 1946, 68, 1592) (3.17 g, 17.7 mmol), 2,4-diamino-5-hydroxymethylpyrimidine (2.50 g, 17.7 mmol), and concentrated hydrochloric acid (2.50 mL) in glacial acetic acid (32 mL) was refluxed for 5 hr. The resulting precipitate was filtered from the cooled reaction mixture and washed with cold acetic acid and ether to give the title compound as tan solid (5.19 g, 79%); mp >290° dec. Anal. Calcd for $C_{14}H_{13}ClN_6.2HCl$: C, 45.00; H, 4.05; N, 22.49; Cl, 28.46. Found: C, 44.89; H, 4.08; N, 22.44; Cl, 28.38.

EXAMPLE 25

A. 5-(8-Diazo-7-methoxy-5-quinolylmethyl)-2,4-(1$\underline{H}$,3$\underline{H}$)pyrimidinedione tetrafluoroborate The product from Example 13C (1.46 g, 4.90 mmol) was suspended in 48% fluoboric acid (15 mL) and cooled to 0°. A solution of sodium nitrite (0.37 g, 5.2 mmol) in water (0.8 mL) was added, keeping the temperature below 5°. A complete solution was obtained, stirred at 0° for 15 min, then poured into ice cold methanol (75 mL) with stirring. The solid that separated was collected, washed with methanol and ether and air dried to give 1.93 g (99%) of the diazonium salt.

B. 5-(7-Methoxy-5-quinolylmethyl)-2,4-(1$\underline{H}$,3$\underline{H}$)pyrimidinedione The product from Example 25A was refluxed in methanol (150 mL) for 45 min. The deep red solution that formed was cooled, neutralized with concentrated ammonium hydroxide, adsorbed onto silica gel and purified by column chromatography with elution by methanol-methylene chloride (1:9) to give the title compound (0.97 g, 70%); mp 302°–304° dec with preliminary darkening. Anal. Calc for $C_{15}H_{13}N_3O_3.0.5H_2O$: C, 61.64; H, 4.83; N, 14.38. Found: C, 61.59; H, 4.59; N, 14.43.

C. 2,4-Dichloro-5-(7-methoxy-5-quinolylmethyl)pyrimidine

The product from Example 25B (0.91 g, 3.2 mmol) was converted to the title compound (0.62 g, 60%) by the procedure of Example 8B. The product was characterized by $^1$H-NMR and mass spectroscopy and used without further purification.

D. 2,4-Diamino-5-(7-methoxy-5-quinolylmethyl)pyrimidine

The product from Example 25C (0.60 g, 1.9 mmol) was converted to the title compound by the procedure of Example 8C. The crude free base (0.39 g, 73%) was recrytallized from 95% ethanol to give off-white solid; mp 275° dec with preliminary darkening. Anal. Calcd for $C_{15}H_{15}N_5O.0.6H_2O$; C, 61.67; H, 5.59; N, 23.97. Found: C, 61.70; H, 5.18; N, 23.98.

EXAMPLE 26

A. 5-(7-Methoxy-8-methylmercapto-5-quinolylmethyl)-2,4-(1$\underline{H}$,3$\underline{H}$)pyrimidinedione The product from Example 25A (1.89 g, 4.80 mmol) was added portionwise to a warm (80°) solution of thiourea (0.50 g, 6.6 mmol) in water (6 mL). After heating for 30 min, the reaction was cooled and the resulting isothiouronium salt was collected and dried (1.53 g, 72%). Without further purification, the salt was added to a solution of sodium bicarbonate (0.58 g, 6.9 mmol) in water (15 mL) and refluxed for 30 min. The dark purple solid that separated was collected, dried (1.16 g, 100%), characterized as 5-(8-mercapto-7-methoxy-5-quinolylmethyl)uracil contaminated with ~20% disulfide. A portion of this solid (0.78 g, 1.97 mmol) was alkylated with methyl iodide (0.28 g, 1.97 mmol) in water (7.5 mL) with 1N sodium hydroxide (2.0 mL, 2.0 mmol). Insolubles were filtered off and the filtrate was taken to pH 6 with acetic acid to precipitate the title compound (0.40 g, 61%); mp 256°–258° dec; structure confirmed by $^1$H-NMR.

B.
2,4-Dichloro-5-(7-methoxy-8-methylmercapto-5-quinolylmethyl)pyrimidine The product of Example 26A (0.27 g, 0.82 mmol) was used in the procedure of Example 8B to give the title compound (0.14 g, 47%).

C.
2,4-Diamino-5-(7-methoxy-8-methylmercapto-5-quinolylmethyl)pyrimidine The product of Example 26C (0.14 g, 0.38 mmol) was used in the procedure of Example 8C to give the title compound as a light yellow solid (0.05 g, 41%), after recrystallization from 95% ethanol; mp 252°–253.5° dec. Anal. Calcd for $C_{16}H_{17}N_5SO$: C, 58.70; H, 5.23; N, 21.39; S, 9.79. Found: C, 58.54; H, 5.28; N, 21.30; S, 9.77.

EXAMPLE 27
5-[7-Allyl-8-(2-methoxyethoxy)-5-quinolylmethyl]-2,4-diaminopyrimidine The product of Example 11A (1.54 g, 5.01 mmol) and 2-methoxyethyl-p-toluenesulfonate (1.15 g, 4.99 mmol) were reacted as in the procedure of Example 1A to give crude product as tan solid (1.83 g). Chromatography on a silica gel column eluted with methanol-methylene chloride (1:4), followed by crystallization from 95% ethanol, gave title compound as white solid (0.77 g, 42%); mp 196°–199.5°. Anal. Calcd for $C_{20}H_{23}N_5O_2$: C, 65.74; H, 6.34; N, 19.16. Found: C, 65.61; H, 6.42; N, 19.36.

EXAMPLE 28
2,4-Diamino-5-(5-amino-6-methyl-8-quinolylmethyl)-pyrimidine dihydrochloride A mixture of 5-amino-6-methylquinoline (2.16 g, 13.7 mmol), prepared by reduction of 6-methyl-5-nitroquinoline (R. Long and K. Schofield, *J. Chem. Soc.* 1953, 2350), 2,4-diamino-5-hydroxymethylpyrimidine (1.91 g, 13.6 mmol), concentrated hydrochloric acid (1.9 mL), and glacial acetic acid was refluxed for 2 hr. The cooled reaction mixture was filtered and the precipitate washed with ether and dried (4.17 g). Recrystallization from aqueous ethanol with hydrochloric acid gave title compound as red-orange solid (2.08 g, 40%); mp >290° dec. Anal. Calcd for $C_{15}H_{16}N_6.2HCl.2H_2O$: C, 46.28; H, 5.70; N, 21.59; Cl, 18.21. Found: C, 46.13; H, 5.61; N, 21.66; Cl, 18.25.

EXAMPLE 29
2,4-Diamino-5-(5-amino-6-methoxy-8-quinolylmethyl)-pyrimidine dihydrochloride A mixture of 5-amino-6-methoxyquinoline (2.50 g, 14.3 mmol), prepared by reduction of 6-methoxy-5-nitroquinoline (H. Decker and H. Engler, *Ber.* 1909, 42, 1740; K. N. Campbell, J. F. Kerwin, A. H. Sommers, and B. K. Campbell, *J. Amer. Chem. Soc.* 1946, 68, 1559; L. Haskelberg, *J. Org. Chem.* 1947, 12, 434) was converted to the title compound by the procedure of Example 28. Recrystallization from aqueous ethanol with hydrochloric acid gave dark red solid (3.34 g, 56%); mp ca. 235° dec. Anal. Calcd for $C_{15}H_{16}N_6O.2HCl.2.5H_2O$: C, 43.49; H, 5.60; N, 20.29; Cl, 17.12. Found: C, 43.55; H, 5.60; N, 20.26; Cl, 17.08.

EXAMPLE 30
2,4-Diamino-5-(8-amino-7-methoxy-5-isoquinolylmethyl)pyrimidine dihydrochloride 8-Amino-7-methoxyisoquinoline (M. Kulka, *J. Amer. Chem. Soc.* 1953, 75, 3597) (1.53 g, 8.80 mmol) was converted to the title compound by the procedure of Example 28. Recrystallization from aqueous ethanol with hydrochloric acid gave dark red solid (0.71 g, 21%); mp >300° dec. Anal. Calcd for $C_{15}H_{16}N_6O.2HCl.0.5H_2O$: C, 47.63; H, 5.06; N, 22.22; Cl, 18.75. Found: C, 47.68; H, 5.06; N, 22.18; Cl, 18.74.

EXAMPLE 31

A.
2,4-Diamino-5-(7,8-Dimethoxy-5-quinolylmethyl)-6-methylthiopyrimidine To a cold (0°) solution of 8-hydroxy-7-methoxyquinoline (0.92 g, 5.25 mmol) and 26% aqueous dimethylamine (3.0 g, 17 mmol) in 10 mL of ethanol was added dropwise 37% aqueous formaldehyde (0.77 g, 9.5 mmol). After stirring at room temperature for 1 hr, the mixture was refluxed for 30 min, cooled and evaporated to dryness. The residue was diluted with water, extracted with ether and dried (MgSO$_4$). Evaporation gave 5-dimethylaminomethyl-8-hydroxy-7-methoxyquinoline as an oil (0.85 g, 69%); structure confirmed by NMR. This oil (0.85 g, 3.6 mmol) was heated under nitrogen with 2,4-diamino-6-methylthiopyrimidine (0.57 g, 3.6 mmol) in ethylene glycol (5 mL) at 140°–165° for 45 min, then cooled. The solid that separated was collected, and washed with ethanol and ether to give 2,4-diamino-5-(8-hydroxy-7-methoxy-5-quinolylmethyl)-6-methylthiopyrimidine as a tan solid (0.47 g, 37%), structure confirmed by NMR and mass spectroscopy. A portion of this solid (0.38 g, 1.1 mmol) was used in the procedure of Example 11B to give the title compound (mp 245°–250° dec). Anal. Calcd for $C_{17}H_{19}N_5SO_2.0.5H_2O$: C, 55.72; H, 5.50; N, 19.11; S, 8.75. Found: C, 55.71; H, 5.51; N, 19.11; S, 8.74.

B.
2,4-Diamino-5-(7,8-dimethoxy-5-quinolylmethyl)-pyrimidine dihydrochloride The product from Example 31A was used in the procedure of Example 17C to give the title compound after recrystallization from ethanol and concentrated hydrochloric acid as a yellow solid; mp 201°–206° with foaming. Anal. Calcd for $C_{16}H_{17}N_5O_2.2HCl.2H_2O$: C, 45.72; H, 5.52; N, 16.66; Cl, 16.87. Found: C, 45.64; H, 5,54; N, 16.59; Cl, 16.76.

EXAMPLE 32

A. Methyl 3,4-dimethoxy-5-(2-propynyloxy)benzoate

Methyl 3,4-dimethoxy-5-hydroxybenzoate (E. Späth and H. Röder, *Mon. f. Chem.* 1922, 43, 93; G. J. Kapadia, Y. N. Vaishnav, M. B. E. Fayez, *J. Pharm. Sci.* 1969, 9, 1157) (0.54 g, 2.54 mmol), propargyl chloride (0.23 g, 3.04 mmol), sodium iodide (3 mg, 0.02 mmol) and potassium carbonate (0.53 g, 3.81 mmol) were refluxed in acetone (10 mL) for 18 hr, cooled, filtered and concentrated. The resulting oil was dissolved in ethyl acetate (20 mL) and washed with water (3×10 mL). The organic layer was dried (Na$_2$SO$_4$), concentrated and recrystllized from alcohol (2.5 mL)/hexane (20 mL) to give methyl 3,4-dimethoxy-5-(2-propynyloxy)-benzoate (0.29 g, 49%); mp 72°–73.5°. Anal. Calcd for C$_{13}$H$_{14}$O$_5$: C, 62.39; H, 5.64. Found: C, 62.28; H, 5.68.

B. Methyl 7,8-dimethoxy-2H-1-benzopyran-5-carboxylate

Methyl 3,4-dimethoxy-5-(2-propynyloxy) benzoate (390 g, 1.56 mol) in N,N-diethylaniline (0.4 L) was refluxed for 40 min. The solution was cooled and diluted with methylene chloride (2 L). The organic solution was extracted with 1N hydrochloric acid (5×1 L), dried (MgSO$_4$) and concentrated to give title compound (390 g, 100%).

A sample recrystallized from ether/hexane gave mp 88.5°–90°; Anal. Calcd for C$_{13}$H$_4$O$_5$: C, 62.39; H, 5.64. Found: C, 62.35; H, 5.68.

C. 7,8-Dimethoxy-5-formyl-2H-1-benzopyran

Methyl 7,8-dimethoxy-2H-1-benzopyran-5-carboxylate (390 g, 1.56 mol) in toluene (1.6 L) was cooled to −15° and a solution of sodium bis(2-methoxyethoxy)aluminum hydride (908 mL, 3.5M in toluene, 3.18 mol) and morpholine (277 g, 3.18 mol) in toluene (900 mL) was added over a 45 min period. After stirring for an additional 30 min, 2N sodium hydroxide solution (2.85 L) was added. The organic layer was separated, washed with 0.8N hydrochloric acid (3×1 L), 5% sodium bicarbonate (500 mL) and water (1 L), dried (MgSO$_4$) and concentrated to give 7,8-Dimethoxy-5-formyl-2H-1-benzopyran (344 g, 86%).

A sample recrystallized from ether/hexane gave mp 82°–82.5°; Anal. Calcd for C$_{12}$H$_{12}$O$_4$: C, 65.44; H, 5.49. Found: C, 65.42; H, 5.51.

D. 2-(7,8-Dimethoxy-2H-1-benzopyran-5-ylmethyl)-3-morpholino-acrylonitrile 7,8-Dimethoxy-5-formyl-2H-1-benzoypyran (362 g, 1.64 mol) in an alcohol/dimethylsulfoxide solution (1.5 L) was added to a refluxing solution of morpholinopropionitrile (299 g, 2.13 mol) and sodium methoxide (115 g, 2.13 mol) in alcohol/dimethylsulfoxide (800 mL) over a 45 min period. The completed reaction mixture was diluted with water (100 mL), concentrated in vacuo to one fourth the original volume and diluted again with water. The resulting solution was extracted with dichloromethane (2×2 L) and the organic phase washed with water (2 L). The organic layer was concentrated and dried by SD3A azeotrope. The resulting oil was used directly in the next step. The NMR is consistent with the assigned structure. TLC shows mixture of E and Z isomers.

E. 2,4-Diamino-5-(7,8-dimethoxy-2H-1-benzopyran-5-ylmethy)pyrimidine 2-(7,8-Dimethoxy-2H-1-benzopyran-5-ylmethyl)-3-morpholino acrylonitrile (562 g, 1.64 mol) and aniline hydrochloride (234 g, 1.80 mol) were refluxed in SD3A (2.4 L) for one hour. The reaction was cooled, and guanidine hydrochloride (313 g, 3.28 mol) and sodium methoxide (275 g, 5.08 mol) were added. After continued reflux, the product crystallized from the cooled reaction mixture. Filtration followed by water wash (2 L) gave 2,4-diamino-5-(7,8-dimethoxy-2H-1-benzopyran-5-ylmethyl)pyrimidine (220 g, 42.7%). Crystallization from ethanol-water gave title compound, mp 235°–238°, identical to the product of Example 1C.

EXAMPLE 33

2,4-Diamino-5-(7,8-dimethoxy-4H-1-benzopyran-5-ylmethyl)pyrimidine 2,4-Diamino-5-(7,8-dimethoxy-2H-1-benzopyran-5-ylmethyl)pyrimidine (3.35 g, 10.6 mmol) and potassium t-butoxide (2.5 g) were warmed in dimethyl sulfoxide (25 mL) at 80° for 1.5 hr. The mixture was diluted with water and filtered. Two fractional crystallizations from 10% acetic acid gave 92% pure 2,4-diamino-5-(7,8-dimethoxy-4H-1-benzopyran-5-ylmethyl)pyrimidine acetate (0.62 g, 18%). The NMR was consistent with the structure with an 8% impurity of 2,4-diamino-5-(7,8-dimethoxy-2H-1-benzopyran-5-ylmethyl)pyrimidine acetate. Anal. calcd for C$_{16}$H$_{18}$N$_4$O$_3$.C$_2$H$_4$O$_2$: C, 57.75; H, 5.92; N, 14.96. Found: C, 57.68; H, 5.93; N, 14.96.

EXAMPLE 34

5-(7-Allyl-8-methoxy-5-[1,2,3,4-tetrahydroquinolyl]methyl)-2,4-diamino pyrimidine To a solution under nitrogen of the product from Example 11B (1.00 g, 3.11 mmol) in glacial acetic acid (20 mL) was added sodium cyanoborohydride (0.79 g, 12.6 mmol). After stirring at room temperature for 18 hr, the reaction was diluted with water (50 mL) and taken to pH 13 with 5N sodium hydroxide. This was extracted with dichloromethane (2×100 mL), washed with water, dried with magnesium sulfate and concentrated to give the title compound as a white solid (0.80 g, 79%); mp 163°–167° after recrystallization from 95% ethanol. Anal. Calcd for C$_{18}$H$_{23}$N$_5$O: C, 66.44; H, 7.12; N, 21.52. Found: C, 66.23; H, 7.20; N, 21.47.

EXAMPLE 35

2,4-Diamino-5-(7-methoxy-8-nitro-5-quinolylmethyl)-pyrimidine

To a cold (5°) solution of 2,4-diamino-5-(7-methoxy-5-quinolylmethyl)pyrimidine (0.28 g, 1.0 mmol) in concentrated sulfuric acid (2 mL) was added dropwise 90% nitric acid (0.10 g, 1.4 mmol). After stirring at 5° for 30 min, the reaction was poured onto ice and the resulting solution taken to pH 3 with 5N sodium hydroxide. The tan solid that separated was collected then boiled in water and filtered to remove insolubles. The filtrate was taken to pH 8 with 1M sodium carbonate to precipitate the title compound (0.14 g, 42%); mp>270° dec. Anal. Calcd for C$_{15}$H$_{14}$N$_6$O$_3$: C, 55.21; H, 4.32; N, 25.75. Found: C, 55.02, H, 4.10; N, 25.41.

EXAMPLE 36

2,4-Diamino-5-(7,8-dimethoxy-2H-1-benzopyran-5-ylmethyl)pyrimidine-1-oxide

To a solution of 2,4-diamino-5-(7,8-dimethoxy-2H-1-benzopyran-5-ylmethyl)pyrimidine (0.993 g, 3.16 mmol) in DMF (80 mL) was added a solution of m-chloroperbenzoic acid (0.641 g, 3.16 mmol as 85%) in DMF (10 mL) dropwise over 30 min. After 18 hr, the solvent was evaporated and the residue chromatographed on silica gel eluted with 10–15% methanol-methylene chloride. Recovered starting material eluted first (0.40 g) followed by title compound as a white powder (0.47 g). Recrystallization from absolute ethanol gave white crystals, mp 233°–234° dec.; assignment of N-1 oxide based on $^{13}$C-NMR: C-4 shifts from 154.40 to 161.28 ppm on acidification. Anal. Calcd for $C_{16}H_{18}N_4O_4$: C, 58.17; H, 5.49; N, 16.96. Found: C, 57.81; H, 6.11; N, 16.84.

EXAMPLE 37

A.
3-(7,8-Dimethoxy-2H-1-benzopyran-5-yl)-2-methoxymethylpropenenitrile

A mixture of sodium methoxide (7.02 g, 0.13 mole), 7,8-dimethoxy-5-formyl-2H-1-benzopyran (57 g, 0.26 mole) and 3-ethoxypropanenitrile (28.35 g, 0.286 mole) in methanol (150 mL) was heated at reflux for 4 hr, allowed to cool and diluted with water (150 mL) and ethylether (500 mL). The layers were separated and the ether portion was washed with water (3×250 mL and 1×100 mL) and dried over magnesium sulfate. The ether solution was concentrated to give 55 g (73%) of an amber oil which was used without further purification.

B.
2,4-Diamino-5-(7,8-dimethoxy-2H-1-benzopyran-5-ylmethyl)pyrimidine

Guanidine hydrochloride (11.46 g, 0.12 mole) in methanol (25 mL) was added to sodium methoxide (6.55 g, 0.12 mole) in methanol (40 mL) and the resultant sodium chloride was filtered and washed with methanol (10 mL). The guanidine solution was added to 3-(7,8-dimethoxy-2H-1-benzopyran-5-yl)-2-methoxymethylpropenenitrile (11.5 g, 0.04 mole) and the mixture heated at reflux for 2 hr. Cooling the mixture at 3° C. provided 5.38 g of yellow solid in two crops. HPLC assayed yield of 28.6%. A sample recrystallized from alcohol/water gave mp 232°–4° C.

EXAMPLE 38

A.
3-(7,8-Dimethoxy-2H-1-benzopyran-5-yl)-2-dimethoxymethylpropanenitrile A mixture of sodium methoxide (8.86 g, 0.164 mole), and 3-(7,8-dimethoxy-2H-1-benzopyran-5-yl)-2-methoxymethylpropenenitrile (Example 37A, 23.1 g, 0.080 mole) in methanol (60 mL) was heated at reflux for 24 hr, allowed to cool and diluted with water (200 mL). The resultant mixture was extracted with toluene (1×200 mL and 2×100 mL). The combined toluene portions were extracted with water (3×100 mL) and dried over magnesium sulfate. The toluene solution was concentrated leaving a brown oil which was distilled under reduced pressure to give 15.9 g (62%) of a yellow oil which was used without further purification.

B.
2,4-Diamino-5-(7,8-dimethoxy-2H-1-benzopyran-5-ylmethyl)pyrimidine

Guanidine hydrochloride (11.94 g, 0.125 mole) and sodium methoxide (6.81 g, 0.126 mole) were combined in methanol (100 mL) and the resulting sodium chloride removed by filtration. The methanolic guanidine solution was added to 3-(7,8-dimethoxy-2H-1-benzopyran-5-yl)-2-dimethoxymethylpropane nitrile (15.9 g, 0.05 mole) and the mixture was heated at reflux for 24 hr. A solution of guanidine, which was prepared from guanidine hydrochloride (4.78 g, 0.05 mole) and sodium methoxide (2.72 g, 0.05 mole), in methanol (25 mL) was added and the mixture heated at reflux for 2 hr additional. On cooling 2.85 g (18%) of 2,4-diamino-5-(7,8-dimethoxy-2H-1-benzopyran-5-ylmethyl)pyrimidine separated, was filtered and dried, mp 233°–4° C. The filtrate was concentrated until a pot temperature of 70° C. was obtained. Heating was continued an additional 2.5 hr, methanol (75 mL) was added and the resultant solid collected by filtration to give 10.4 g of light colored solid. Total HPLC assayed yield of 60.3% was obtained. A sample recrystallized from alcohol/water gave mp 236° C.

EXAMPLE 39

A. Ethyl 2-cyano-3-(7,8-dimethoxy-2H-1-benzopyran-5-yl)propenoate

A mixture of ethylcyanoacetate (11.3 g, 0.1 mole), 7,8-dimethoxy-5-formyl-2H-1-benzopyran (22.0 g, 0.1 mole), piperidine (1.02 g, 0.01 mole) and acetic acid (0.36 g, 0.006 mole) in benzene (100 mL) was heated at reflux for 5 hr with azeotropic removal of water and allowed to cool. The solution was extracted successively with water (200 mL), 0.5N hydrochloric acid (200 mL), saturated sodium bicarbonate solution (200 mL), $H_2O$ (200 mL) and dried over magnesium sulfate. The volatiles were removed under reduced pressure to give 21.1 g (66.9%) of an orange solid, mp 104.5°–107.5° C.

B. Ethyl 2-cyano-3-(7,8-dimethoxy-2H-1-benzopyran-5-yl)propanoate

A mixture of ethyl 2-cyano-3-(7,8-dimethoxy-2H-1-benzopyran-5-yl)propenoate (19.8 g, 0.63 mole) in ethanol (500 mL) under nitrogen was treated with acetic acid (4 mL) and a trace of bromocresol green and heated to reflux. Heating was discontinued and sodium cyanoborohydride (4.4 g, 0.07 mole) in ethanol (100 mL) was co-added with additional acetic acid (11 mL). The mixture was stirred under nitrogen for 2 hr, acetic acid (10 mL) added and the ethanol removed under reduced pressure. The resultant yellow solid was taken up in ethyl acetate (250 mL) and successively extracted with water (125 mL), saturated sodium bicarbonate (3×100 mL) and water (100 mL), then dried over magnesium sulfate. The volatiles were removed under reduced pressure to leave an amber oil, 18.22 g (91.4%) which was used without further purification.

C. 2,4-Diamino-5-(7,8-dimethoxy-2H-1-benzopyran-5-ylmethyl)pyrimidine

A mixture of ethyl 2-cyano-3-(7,8-dimethoxy-2H-1-benzopyran-5-yl)propanoate (3 g, 0.0095 mole) and diethoxymethylacetate (4.86 g, 0.03 mole) was heated at 130°–140° C. for 20 hr under a steam jacketed condenser, stripped under high vacuum, 0.1 mm Hg, to a viscous oil and recharged with diethoxymethyl acetate (4.86 g, 0.03 mole). The mixture was heated as before for 24 hr and concentrated to a gum under high vacuum (0.1 mm). The gum was dissolved in ethanolic potassium hydroxide (0.66 g [85%], 0.01 mole in 25 mL) and the resultant solution heated at reflux for 2 hr. Guanidine, which was prepared by combining guanidine hydrochloride (3.34 g, 0.035 mole) in absolute ethanol (20 mL) with sodium methoxide. (1.9 g, 0.035 mole) in absolute ethanol (30 mL) and filtering the resultant sodium chloride, was then added to the hot ethanolic potassium hydroxide solution. Ethanol was boiled out of the mixture until a pot temperature of 85° C. was achieved. Reflux was then maintained for 18 hr and the mixture allowed to cool. The resultant precipitate was filtered, washed with cold ethanol (20 mL) and dried under reduced pressure to yield 2.42 g of light brown solid. HPLC assayed yield was 27%. A sample recrytstallized from alcohol/water gave mp 235° C.

EXAMPLE 40

Biological Data (A) MIC Table 1

| Organisms | Minimum Inhibitory Concentrations (μg/ml) of selected compounds | | | | | | |
|---|---|---|---|---|---|---|---|
| | TMP | 1 | 4 | 8 | 9 | 25 | 31 |
| St. faecalis CN478 | 0.1 | 0.05 | 0.01 | 0.1 | 0.05 | 0.05 | 0.05 |
| St. agalactiae CN1143 | 0.5 | 0.05 | 0.05 | 0.1 | 0.5 | 0.05 | 0.5 |
| Staph. aureus CN491 | 0.5 | 0.05 | 0.05 | 0.1 | 0.5 | 0.05 | 0.05 |
| Vibrio cholerae ATCC14035 | 0.5 | 0.05 | 0.05 | 0.05 | 0.5 | 0.05 | 0.05 |
| Esch. coli CN314 | 0.05 | 0.05 | 0.1 | 0.1 | 0.1 | 0.05 | 0.1 |
| Pr. mirabilis S2409 | 5.0 | 5 | 5.0 | 1.0 | 5.0 | 5.0 | 5.0 |
| Meningococci (average 5 strains) | 18.0 | 3.1 | 2.8 | 3.7 | >25 | 3.1 | 14.4 |
| Gonococci (average 17 strains) | 37.1 | 10.0 | 4.6 | 11.1 | >25 | 8.1 | 34.4 |
| B. fragilis (average 3–10 strains) | 4.0 | 1.08 | 0.48 | 5.2 | 7.8 | 2.6 | 3.1 |

(B) MIC Table 2

| Compound | MIC (μg/ml) vs Staph. aureus | Compound | MIC (μg/ml) vs Staph. aureus |
|---|---|---|---|
| TMP | 0.5 | | |
| 2 | 0.5 | | |
| | | 27 | 0.1 |
| 3 | 0.5 | 28 | 0.1 |
| 5 | 0.5 | 29 | 0.5 |
| 6 | 0.05 | 30 | 0.1 |
| 7 | 0.5 | 32 | — |
| 10 | 0.05 | 33 | — |
| 11 | 1.0 | | |
| 12 | 0.05 | | |
| 13 | 0.1 | 34 | 5.0 |
| 14 | 0.05 | 35 | 0.5 |
| 15 | 0.5 | | |
| 16 | 0.05 | | |
| 17 | 0.5 | | |
| 18 | 0.5 | | |
| 19 | 0.05 | | |
| 20 | 0.05 | | |
| 36 | 0.05 | | |
| 22 | 0.1 | | |
| 23 | 5.0 | | |
| 24 | 0.1 | | |
| 26 | 0.05 | | |

(C) Toxicity

| Compound 1: | Acute LD$_{50}$ i.p. mouse = 610 mg/Kg |
|---|---|
| | p.o. rat = >1000 mg/Kg |
| 8: | Acute LD$_{50}$ i.p. mouse = 500 mg/Kg |

EXAMPLE 41

Tablets

| Ingredient | Amount per tablet (mg) | |
|---|---|---|
| | Single Active Ingredient | Combination |
| 2,4-Diamino-5-(7,8-dimethoxy-2$\underline{H}$-1-benzopyran-5-ylmethyl)-pyrimidine | 100.0 | 80.0 |
| Sulfamethoxazole | — | 400.0 |
| Lactose | 84.0 | 100.0 |
| Potato starch, dried | 14.3 | 18.0 |
| Magnesium stearate | 0.7 | 1.0 |
| Polyvinylpyrrolidone | 1.0 | 1.0 |

The 2,4-diamino-5-(7,8-dimethoxy-2$\underline{H}$-1-benzopyran-5-ylmethyl)pyrimidine, lactose and potato starch (and sulfamethoxazole in the combination formulation) are mixed together and then granulated with aqueous polyvinylpyrrolidone. The granules are dried, mixed with the magnesium stearate and then compressed to produce tablets weighing 200 mg each (single active ingredient) or 600 mg each (combination).

EXAMPLE 42

Capsules

| Ingredient | Amount per capsule (mg) | |
|---|---|---|
| | Single Active Ingredient | Combination |
| 2,4-Diamino-5-(7-methoxy-8-methylthio-5-quinolylmethyl)-pyrimidine | 100.0 | 80.0 |
| Sulfisoxazole | — | 160.0 |
| Lactose | 149.0 | 79.0 |
| Corn starch | 149.0 | 79.0 |
| Stearic acid | 2.0 | 2.0 |

The ingredients are thoroughly mixed and then loaded into hard gelatin capsules containing 400 mg each.

EXAMPLE 43

Capsules

| Ingredient | Amount per ampoule |
|---|---|
| 2,4-Diamino-5-(8-dimethylamino-7-methyl-5-quinolylmethyl)pyrimidine dihydrochloride | 5.0 mg |
| Water for injection, q.s. to | 1.0 ml |

The 2,4-diamino-5-(8-dimethylamino-7-methyl-5-quinolylmethyl)pyrimidine dihydrochloride is dissolved in the water and the solution sterilized by ultrafiltration. The sterile solution is delivered into sterile capsules and the ampoules sealed, the entire operation being carried out under sterile conditions.

EXAMPLE 44

Suspension

| Ingredient | Amount per 5 ml |
|---|---|
| 2,4-Diamino-5-(8-amino-7-methoxy-5-quinolylmethyl)-pyrimidine dihydrochloride | 40.0 mg |
| Sulfamethizole | 200.0 mg |

-continued

| Ingredient | Amount per 5 ml |
|---|---|
| Microcrystalline cellulose | 110.0 mg |
| Sodium carboxymethylcellulose | 10.0 mg |
| Methyl paraben | 3.0 mg |
| Propyl paraben | 2.0 mg |
| Polysorbate 80 | 5.0 mg |
| Sucrose | 3.5 g |
| Flavor | q.s. |
| Color | q.s. |
| Alcohol | q.s. |
| Purified water, q.s. to | 5.0 ml |

The microcrystalline cellulose and sodium carboxymethylcellulose are added to a portion of the water. The sucrose is then added and dissolved therein. The Polysorbate 80 (a polyethylene oxide sorbitan monooleate) is then mixed into the suspension. A solution of the methyl paraben, propyl paraben, flavor and color in a minimal amount of alcohol is then added. The finely ground active ingredients (2,4-diamino-5-(8-amino-7-methyl-5-quinolylmethyl)pyrimidine dihydrochloride and sulfamethizole) are then added. Sufficient water is then added to bring the volume to 5.0 ml and the suspension is thoroughly mixed.

Potentiation study:
2,4-diamino-5-(7,8-dimethoxy-2H-1-benzopyran-5-ylmethyl)pyrimidine (compound 1) and sulphamethoxazole (SMX)

A. Materials and methods

1. Bacterial strains. The bacteria employed in this study are listed in Table 1.

2. Compound Preparation. Compound 1, trimethoprim (TMP) and SMX were each treated with N,N-dimethylformamide for 30 minutes. Dilutions were prepared using sterile distilled water.

3. Testing procedure. Two checkerboard patterns were set-up, namely: 1. SMX and TMP-lactate and 2. SMX and compound 1-lactate. Thirteen, two-fold dilutions of compound 1-lactate were prepared with final concentrations ranging from 6.2 ug/ml to 0.0016 ug/ml. Twenty two, two-fold dilutions of SMX were prepared with final plate concentrations ranging from 31 ug/ml to 0.000016 ug/ml. An analogous checkerboard scheme was set-up for the combination TMP and SMX. Microorganisms were grown on Wellcotest Sensitivity Test Agar containing various concentrations and permutations of compounds.

From the MIC's, a fractional inhibitory concentration (FIC) was calculated. This involves determining a fraction by dividing the MIC of an agent in combination over the MIC of the agent alone (1). If it is less than one, the interaction is synergistic, and if the sum is greater than one, the combination is antagonistic.

B. Results and Discussion:

Table 1 summarizes the results derived from the two checkerboard experiments indicating the lowest FIC index for each organism tested and the MIC ratio of the drug combinations corresponding to the FIC index. On the basis of these data, particularly the FIC indices, SMX appears to potentiate compound 1 as well as it does TMP in an in vitro situation. It should be noted that Norden et al. (2) have demonstrated a lack of correlation between the Berenbaum criteria (1) and other methods of assaying synergy. This per se, does not invalidate this analytic approach, however, since there is no absolute standard for establishing synergistic interations (3). Under the experimental conditions and definitions outlined above, in vitro potentation can be demonstrated between SMX and compound 1 in the case of four individual gram negative microorganisms and one isolate of S aureus.

C. References:

1. Berenbaum, M. C. 1978. A method for testing for synergy with any number of agents. J. Inf. Dis. 137: 122–130.

2. Norden, C. W. et al. 1979. Comparison of techniques for measurement of in vitro antibiotic synergism. J. Inf. Dis. 140: 629–633.

3. Young, L. S. 1980. Antimicrobial synergy testing. Clin.Micro. Newletter 2: 1–3.

TABLE 1

| | Summary of the compound 1/SMX and TMP/SMX checkerboard experiments. | | | |
|---|---|---|---|---|
| ORGANISM | FIC INDEX COMPOUND 1/SMX | MIC RATIO COMPOUND 1/SMX | FIC INDEX TMP/SMX | MIC RATIO TMP/SMX |
| E. cloi CN314 | 0.12 | 0.0125/2.0 | 0.18 | 0.0125/2.0 |
| S. aureus CN491 | 0.12 | 0.0031/1.0 | 0.12 | 0.025/1.0 |
| P. vulgaris CN329 | 0.12 | 0.05/1.0 | 0.12 | 0.1/0.5 |
| P. vulgaris P69 | 0.18 | 0.4/0.25 | 0.16 | 0.1/1.0 |
| P. vulgaris P70 | 0.09 | 0.1/1.0 | 0.08 | 0.2/0.25 |

Comparison between trimethoprim (TMP) and 2,4-diamino-5-(7,8-dimethoxy-2H-1-benzopyran-5-ylmethyl)pyrimidine compound 1 in experimental salmonellosis in calves.

Twenty-six calves. 3 weeks old, were orally dosed with a culture of Salmonella dublin by a method which had previously been shown to induce symptoms closely resembling naturally occuring acute salmonellosis in calves, with a mortality rate of about 90%, white et al 1981(a) Rs Vet sci 31 19–26. The calves were divided into four groups, each of 6 or 7 calves, and, beginning two days after infection, and continuing for a total of 5 conservative days, the calves in groups 1 to 3 were given daily injections of sulphadiozine (SDZ) plus either trimethoprim (TMP) or compound 1 at the dose takes shown in the table, which also shows that the final mortality results.

It has previously been demonstrated that SDZ alone, even at 40 mg/kg/day, has no effect on mortality in this disease model white et al 1981(b) Rs Vet sci 31, 19–26, and therefore the low mortality results in groups 1 to 3 are a to the simultaneous administration of the benzylpyrimidine. In this respect, compound 1 at 1 mg/kg (group 2) was clearly superior to TMP at 1 mg/kg (group 1), further evidence being provided by the much more rapid recovery of the survivors in group 2 in comparison with those in group 1. Even 0.5 mg/kg of compound 1 (group 3) produced a reduction of mortality comparable with that in group 1 (TMP, 1 mg/kg), and it was therefore concluded that compound 1 was approximately twice as effective as TMP in this disease syndrome in calves.

| Group | No. of calves | Daily dosage (mg/kg) of | | | Mortality |
|---|---|---|---|---|---|
| | | TMP | Compound 1 | SDZ | |
| 1 | 7 | 1 | — | 20 | 2/7 |
| 2 | 6 | — | 1 | 20 | 0/6 |
| 3 | 7 | — | 0.5 | 20 | 3/7 |
| 4 | 6 | — | — | — | 6/6 |

We claim:
1. A compound of formula (VIII):

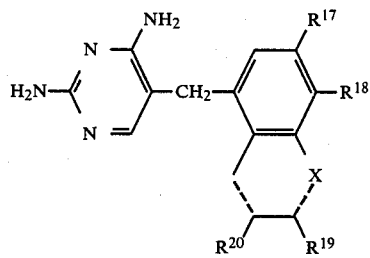

or a pharmaceutically acceptable salt thereof, wherein $R^{17}$ and $R^{18}$ together form a methylene-dioxy group or $R^{17}$ is hydrogen, halogen, $C_{1-4}$ alkyl, $C_{1-4}$ alkoxy, $C_{2-4}$ alkenyl, amino, trifluoromethyl, a group $-COR^{21}$ wherein $R^{21}$ is $C_{1-4}$ alkyl or $C_{1-4}$ alkoxy, or a group $-OSO_2R^{22}$ wherein $R^{22}$ is $C_{1-4}$ alkyl; $R^{18}$ is halogen, $C_{1-4}$ alkyl, $C_{2-4}$ alkenyl, hydroxy, amino, mono- or di-$C_{1-4}$ alkyl substituted amino, mercapto-, $C_{1-4}$ alkylthio, trifluoromethyl, a group $-COR^{21}$ or a group $-OSO_2R^{22}$ wherein $R^{21}$ and $R^{22}$ are as hereinbefore defined; $R^{19}$ is hydrogen, $=O$, S, $(CH_3)_2$, halogen, $C_{1-4}$ alkyl; $R^{20}$ is hydrogen or methyl, X is oxygen or nitrogen and the dotted lines represent single or double bonds with the exception that when X is an oxygen atom the dotted line adjacent to it cannot represent a double bond.

2. A compound of formula (IV):

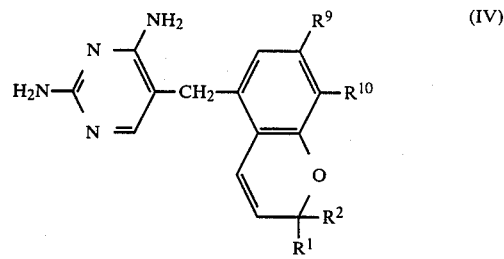

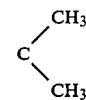

or a pharmaceutically acceptable salt thereof wherein $R^1$ and $R^2$ are hydrogen, halogen, $C_{1-4}$ alkyl, $C_{1-4}$ alkylthio or $C_{1-4}$ alkoxy or $R^1$ and $R^2$ are linked to the same carbon atom to form a group $C=O$, $C=S$ or $$C{<}^{CH_3}_{CH_3}$$

$R^9$ and $R^{10}$ are hydrogen, halogen, $C_{2-4}$ alkenyl, $C_{2-4}$ alkenyloxy, nitro or $NR^{11}R^{12}$ wherein $R^{11}$ and $R^{12}$ are hydrogen, methyl or ethyl except that $R^9$ and $R^{10}$ are not both hydrogen or halogen.

* * * * *